(12) United States Patent
Boles et al.

(10) Patent No.: US 8,993,301 B2
(45) Date of Patent: Mar. 31, 2015

(54) VECTOR WITH CODON-OPTIMISED GENES FOR AN ARABINOSE METABOLIC PATHWAY FOR ARABINOSE CONVERSION IN YEAST FOR ETHANOL PRODUCTION

(71) Applicant: Johann Wolfgang Goethe—Universitaet Frankfurt am Main, Frankfurt am Main (DE)

(72) Inventors: Eckhard Boles, Darmstadt (DE); Beate Rother, Einbeck (DE)

(73) Assignee: Butalco GmbH, Hünenberg (CH)

(*) Notice: Subject to any disclaimer, the term of this patent is extended or adjusted under 35 U.S.C. 154(b) by 0 days.

(21) Appl. No.: 14/231,061

(22) Filed: Mar. 31, 2014

(65) Prior Publication Data

US 2014/0206070 A1 Jul. 24, 2014

Related U.S. Application Data

(63) Continuation of application No. 12/531,988, filed as application No. PCT/EP2008/002277 on Mar. 20, 2008, now Pat. No. 8,753,862.

(30) Foreign Application Priority Data

Apr. 5, 2007 (DE) .................. 10 2007 016 534

(51) Int. Cl.
| | | |
|---|---|---|
| C12N 9/90 | (2006.01) | |
| C12N 15/00 | (2006.01) | |
| C12N 1/14 | (2006.01) | |
| C07H 21/04 | (2006.01) | |
| C07H 21/00 | (2006.01) | |
| C12N 9/00 | (2006.01) | |
| C12N 15/81 | (2006.01) | |
| C12P 7/10 | (2006.01) | |
| C12N 1/18 | (2006.01) | |

(52) U.S. Cl.
CPC ...... *C07H 21/00* (2013.01); *C12N 9/00* (2013.01); *C12N 15/81* (2013.01); *C12P 7/10* (2013.01); *C12N 1/18* (2013.01); *C12N 15/00* (2013.01); *Y02E 50/16* (2013.01); *Y02E 50/17* (2013.01)
USPC ............... 435/233; 435/320.1; 435/254.21; 435/440; 536/23.2

(58) Field of Classification Search
CPC ......... C12N 9/90; C12N 15/80; C12N 15/815
See application file for complete search history.

(56) References Cited

U.S. PATENT DOCUMENTS

| 6,030,807 A | 2/2000 | De Lencastre et al. |
| 8,129,171 B2 | 3/2012 | Boles et al. |
| 2005/0142648 A1 | 6/2005 | Boles et al. |

FOREIGN PATENT DOCUMENTS

| WO | WO 98/50524 | 11/1998 |
| WO | WO 03/008593 | 1/2003 |
| WO | WO 2006/096130 | 9/2006 |

OTHER PUBLICATIONS

Nolling et al. AE001437. 2001.*
Nolling et al. Q97JE0. 2001.*
Bennetzen, Jeffrey L. et al., "Codon Selection in Yeast," *The Journal of Biological Chemistry*, Mar. 25, 1982, vol. 257, No. 6, p. 3026-3031.
Branden, Carl et al., "Prediction, Engineering, and Design of Protein Structures," *Introduction to Protein Structure*, 1991, Garland Publishing, Inc., New York, p. 247.
Database NCBI, "AraA, *Bacillus licheniformis*," Sep. 29, 2004, Database Accession No. AAU41894.
Fonseca, César et al., "L-Arabinose transport and catabolism in yeast," *The FEBS Journal*, 2007, vol. 274, p. 3589-3600.
Nölling, Jörk et al., "Genome Sequence and Comparative Analysis of the Solvent-Producing Bacterium *Clostridium acetobutylicum*", *Journal of Bacteriology*, Aug. 2001, vol. 183, No. 16, p. 4823-4838.
Sedlak, Miroslav et al., "Expression of *E. coli* araBAD operon encoding enzymes for metabolizing L-arabinose in *Saccharomyces cerevisiae*," *Enzyme and Microbial Technology*, 2001, vol. 28, p. 16-24.
UnitProt Database—Q65GC0—2004.
UnitProt Database—Q97JE4—2001.
UnitProtKB Database—ARAA1_BACLD—2007.
Veith, Birgit et al., "The Complete Genome Sequence of *Bacillus licheniformis* DSM13, An Organism with Great Industrial Potential", *Journal of Molecular Microbiology and Biotechnology*, Sep. 2004, vol. 7, No. 4, pp. 204-211.

* cited by examiner

*Primary Examiner* — Yong Pak
(74) *Attorney, Agent, or Firm* — Saliwanchik, Lloyd & Eisenschenk

(57) ABSTRACT

The present invention relates to novel expression cassettes and expression vectors, comprising three nucleic acid sequences for araA, araB and araD, each coding for a polypeptide of an L-arabinose metabolic pathway, in particular, a bacterial L-arabinose metabolic pathway. The invention particularly relates to expression cassettes and expression vectors, comprising codon-optimized nucleic acid sequences for araA, araB and araD. The invention further relates to host cells, in particular modified yeast strains containing the expression cassettes or expression vectors and expressing the polypeptides for the L-arabinose metabolic pathway, in particular, for the bacterial L-arabinose metabolic pathway. When using these modified host cells, arabinose is more effectively fermented by these cells, in particular into ethanol. The present invention is therefore relevant, inter alia, in connection with the production of biochemicals from biomass, such as bioethanol for example.

15 Claims, 9 Drawing Sheets

US 8,993,301 B2

VECTOR WITH CODON-OPTIMISED GENES FOR AN ARABINOSE METABOLIC PATHWAY FOR ARABINOSE CONVERSION IN YEAST FOR ETHANOL PRODUCTION

CROSS REFERENCE TO A RELATED APPLICATION

This application is a continuation application of co-pending application Ser. No. 12/531,988, filed Jan. 19, 2010; which is a National Stage Application of International Application Number PCT/EP2008/002277, filed Mar. 20, 2008; which claims priority to German Patent Application No. 102007016534.1, filed Apr. 5, 2007; all of which are incorporated herein by reference in their entirety.

The Sequence Listing for this application is labeled "January2010-ST25.txt", which was created on Oct. 6, 2009, and is 19 KB. The entire contents is incorporated herein by reference in its entirety.

FIELD OF THE INVENTION

The present invention relates to novel expression cassettes and expression vectors, comprising three nucleic acid sequences for araA, araB and araD, each coding for a polypeptide of an L-arabinose metabolic pathway, in particular, a bacterial L-arabinose metabolic pathway. The invention particularly relates to expression cassettes and expression vectors, comprising codon-optimised nucleic acid sequences for araA, araB and araD. The invention further relates to host cells, in particular modified yeast strains containing the expression cassettes or expression vectors and expressing the polypeptides for the L-arabinose metabolic pathway, in particular, for the bacterial L-arabinose metabolic pathway. When using these modified host cells, arabinose is more effectively fermented by these cells, in particular into ethanol. The present invention is therefore relevant, inter alia, in connection with the production of biochemicals from biomass, such as bioethanol for example.

BACKGROUND OF THE INVENTION

The beer, wine and baking yeast *Saccharomyces cerevisiae* has already been used for centuries for the production of bread, wine and beer owing to its characteristic of fermenting sugar to ethanol and carbon dioxide. In biotechnology, *S. cerevisiae* is used particularly in ethanol production for industrial purposes, in addition to the production of heterologous proteins. Ethanol is used in numerous branches of industry as an initial substrate for syntheses. Ethanol is gaining increasing importance as an alternative fuel, due to the increasingly scarce presence of oil, the rising oil prices and continuously increasing need for petrol worldwide.

In order to produce bioethanol inexpensively and efficiently, the use of lignocellulose-containing biomass, such as for example straw, waste from the timber industry and agriculture and the organic component of everyday household waste, presents itself as an initial substrate. Firstly, said biomass is very convenient and secondly is present in large quantities. The three major components of lignocellulose are lignin, cellulose and hemicellulose. Hemicellulose, which is the second most frequently occurring polymer after cellulose, is a highly branched heteropolymer. It consists of pentoses (L-arabinose, D-xylose), uronic acids (4-O-methyl-D-glucuronic acid, D-galacturonic acid) and hexoses (D-mannose, D-galactose, L-rhamnose, D-glucose) (see FIG. 1). Although, hemicellulose can be hydrolized more easily than cellulose, but it contains the pentoses L-arabinose and D-xylose, which can normally not be converted by the yeast *S. cerevisae*.

In order to be able to use pentoses for fermentations, these must firstly enter the cell through the plasma membrane. Although *S. cerevisiae* is not able to metabolize D-xylose, it can uptake D-xylose into the cell. However, *S. cerevisiae* does not have a specific transporter. The transport takes place by means of the numerous hexosetransporters. The affinity of the transporters to D-xylose is, however, distinctly lower than to D-glucose (Kotter and Ciriacy, 1993). In yeasts which are able to metabolize D-xylose, such as for example *P. stipitis*, *C. shehatae* or *P. tannophilus* (Du Preez et al., 1986), there are both unspecific low-affinity transporters, which transport D-glucose, and also specific high-affinity proton symporters only for D-xylose (Hahn-Hagerdal et al., 2001).

In earlier experiments, some yeasts were found, such as for example *Candida tropicalis, Pachysolen tannophilus, Pichia stipitis, Candida shehatae*, which by nature ferment L-arabinose or can at least assimilate it. However, these yeast lack entirely the capability of fermenting L-arabinose to ethanol, or they only have a very low ethanol yield (Dien et al., 1996).
Conversion of L-arabinose In order for the pentose L-arabinose to be metabolised by *S. cerevisiae*, it must enter into the cell via transport proteins and be converted to the metabolite D-xylulose-5-phosphate in three enzymatic steps. These three enzymatic steps may be made available to the yeast by heterologously expressed genes. D-xylulose-5-phosphate functions as an intermediate of the pentose phosphate pathway and can be decomposed further to yield ethanol under anaerobic conditions in the cell (see FIG. 2).

Becker and Boles (2003) describe the engineering and the selection of a laboratory strain of *S. cerevisiae* which is able to use L-arabinose for growth and for fermenting it to ethanol. This was possible due to the over-expression of a bacterial L-arabinose metabolic pathway, consisting of *Bacillus subtilis* AraA and *Escherichia coli* AraB and AraD and simultaneous over-expression of yeast galactose permease transporting L-arabinose in the yeast strain. Molecular analysis of the selected strain showed that the predetermining precondition for a use of L-arabinose is a lower activity of L-ribulokinase. However, inter alia, a very slow growth is reported from this yeast strain (see FIG. 2).

So far, it was only possible to express the native genes of bacterial arabinose metabolic pathways that are essential for metabolising arabinose in *S. cerevisiae* on single plasmids or to integrate them individually in the yeast genome, respectively (Karhumaa et al, 2006). This means that each yeast transformant with a functional arabinose metabolic pathway contained at least three plasmids or the genes integrated into the rDNA locus (Becker and Boles, 2003; Karhumaa et al, 2006).

The presence of the genes on different plasmids is associated with a number of disadvantages. On the one hand, plasmids that are present simultaneously represent additional stress for the yeast cells ("Plasmid stress", Review of *E. coli* by Bailey (1993)). On the other hand, the plasmids used have strong homologies in their sequences, which can lead to loss of information within the plasmids due to homologous recombination (Wiedemann, 2005). However, the main disadvantages associated with the use of plasmids lie in the fact that they remain unstable in the strains without selection pressure and that they are not suitable for industrial use.

Moreover, it would be ideal for industrial applications if the microorganism used were able to metabolise all of the sugars present in the medium. Since the yeasts currently used industrially are not capable of metabolising the arabinose in the medium, it would be highly advantageous to provide the strains with this additional capability in a stable manner.

The object of the present invention is therefore to provide means that overcome the disadvantages known from the prior art of introducing genes of a bacterial L-arabinose metabolic pathway into host cells individually, and which in particular may be usable for industrial yeast strains.

BRIEF SUMMARY

The object is solved according to the invention by the provision of nucleic acid molecules comprising three nucleic acid sequences, each of which codes for a polypeptide of an L-arabinose metabolic pathway, in particular a bacterial L-arabinose metabolic pathway.

A nucleic acid molecule according to the invention is a recombinant nucleic acid molecule. Furthermore, nucleic acid molecules according to the invention comprise dsDNA, ssDNA, PNA, CNA, RNA or mRNA, or combinations thereof.

DETAILED DESCRIPTION OF THE INVENTION

The "L-arabinose metabolic pathway" or "bacterial L-arabinose metabolic pathway", such as it occurs in *E. coli*, is shown in FIG. 2. This metabolic pathway contains 3 enzymes: L-arabinose isomerase, L-ribulokinase and L-ribulose-5-P-4-epimerase. The genes that code for these enzymes are called araA, araB and araD. L-arabinose isomerase converts L-arabinose to L-ribulose, which is further metabolised to L-ribulose-5-phosphate by the L-ribulokinase. Finally, the L-ribulose-5-P-4-epimerase converts L-ribulose-5-phosphate to D-xylulose-5-phosphate. The intermediate metabolite D-xylulose-5-phosphate is formed by the heterologously expressed genes of the L-arabinose metabolic pathway, particularly the bacterial L-arabinose metabolic pathway, in the yeast cell. D-xylulose-5-phosphate functions as an intermediate of the pentose phosphate pathway and can be further decomposed to ethanol under anaerobic conditions in a yeast cell. Enzymes of the xylose metabolic pathway are also found in fungi, and these and other enzymes isolated from eukaryotes can also be used as enzymes for the L-arabinose metabolic pathway.

The three nucleic acid sequences of the nucleic acid molecules according to the invention, each of which codes for a polypeptide of an L-arabinose metabolic pathway, are preferably araA (L-arabinose isomerase), araB (L-ribulokinase) and araD (L-ribulose-5-P-4-epimerase).

The nucleic acid molecules according to the invention preferably comprise nucleic acid sequences that are identical with the naturally occurring nucleic acid sequence or that have been codon-optimised for use in a host cell.

Each amino acid is encoded by one codon. However, there are several different codons that code for an individual amino acid. The genetic code is, thus, degenerated. The preferred codon selection for a corresponding amino acid varies from one organism to another. For example, problems may arise in heterologously expressed genes if the host organism or host cell has a very different codon usage. The gene can only be expressed very slowly, if at all. Differing codon usage may even be observed in genes of different metabolic pathways within the same organism. The glycolysis genes from *S. cerevisiae* are known to be expressed strongly. They have a highly restrictive codon usage. Adapting the codon usage of the bacterial genes of the arabinose metabolic pathway to the codon usage of the glycolysis genes from *S. cerevisiae* leads to improved arabinose metabolism in yeast.

For codon optimisation, the inventors did not rely on the usual platforms of synthetic gene designers for heterologous expression (such as Synthetic Gene Designer as described in Wu et al. 2006), instead they adapted the codon optimisation specifically to the codon usage of the glycolysis genes in the yeast. The glycolysis genes in the yeast have a highly restrictive codon usage, which is aligned with the frequency of the corresponding tRNA. The glycolysis genes use mainly codons for which there are high concentrations of the corresponding tRNAs, which in turn results in greater translation efficiency and gene expression (Bennetzen and Hall, 1982, Hoekema et al., 1987). In contrast, the usual synthetic gene designers are geared more to the average codon usage of all the genes in an organism, not just those that are highly expressed, and they also take into account other factors, such as stability. Accordingly, codon optimisation with the aid of such an electronic platform, such as the one described in Wu et al. 2006, results in a nucleic acid sequence that is entirely different from the one disclosed in this patent specification.

According to the invention, at least two of the three nucleic acid sequences, and preferably all three nucleic acid sequences, have been codon optimised for use in a host cell.

The nucleic acid sequence for araB (L-ribulokinase) and the nucleic acid sequence for araD (L-ribulose-5-P-4-epimerase) are preferably derived from *E. coli*. Thereby, the nucleic acid sequence for araB preferably comprises a nucleic acid sequence with SEQ ID NO: 1 and the nucleic acid sequence for araD preferably comprises a nucleic acid sequence with SEQ ID NO: 2.

The nucleic acid sequence with SEQ ID NO: 1 is the gene sequence of the open reading frame (ORF) of araB$^{mut}$ from *E. coli* in a codon-optimised form.

The nucleic acid sequence with SEQ ID NO: 2 is the gene sequence of the open reading frame (ORF) of araD from *E. coli* in a codon-optimised form.

The nucleic acid sequence for araA (L-arabinose isomerase) is preferably derived from *Bacillus licheniformis* or *Clostridium acetobutylicum*.

These L-arabinose isomerases are advantageous for the growth of yeast transformants on an arabinose medium. Example 1 shows (see also FIG. 4) that, compared with the isomerase from *B. subtilis*, particularly the expression of the L-arabinose isomerase from *C. acetobutylicum* and *B. licheniformis* significantly improved the growth of yeast transformants on arabinose medium.

Thereby, the nucleic acid sequence for araA preferably comprises a nucleic acid sequence with SEQ ID NO: 3, 4 or 5.

The nucleic acid sequence with SEQ ID NO: 3 is the gene sequence of the open reading frame (ORF) of araA from *Bacillus licheniformis* in a codon-optimised form.

The nucleic acid sequence with SEQ ID NO: 4 is the gene sequence of the open reading frame (ORF) of araA from *Bacillus licheniformis*.

The nucleic acid sequence with SEQ ID NO: 5 is the gene sequence of the open reading frame (ORF) of araA from *Clostridium acetobutylicum*.

Accordingly, the nucleic acid sequences with SEQ ID NOs: 4 and 5 are naturally occurring nucleic acid sequences.

In a particularly preferred embodiment, a nucleic acid molecule according to the invention comprises the nucleic acid sequence with SEQ ID NO: 1, the nucleic acid sequence with SEQ ID NO: 2 and the nucleic acid sequence with SEQ ID NO: 3, 4 or 5. Most preferable is a nucleic acid molecule according to the invention that comprises the nucleic acid sequence with SEQ ID NO: 1, the nucleic acid sequence with SEQ ID NO: 2, and the nucleic acid sequence with SEQ ID NO: 3.

Yeast transformants that have the two codon-optimised genes of the kinase (araB, SEQ ID NO: 1) and the epimerase (araD, SEQ ID NO: 2), and yeast transformants in which all three genes have been codon-optimised (araB: SEQ ID NO: 1, araD: SEQ ID NO: 2 and araA: SEQ ID NO: 3), show a considerable growth advantage in a medium containing arabinose compared to yeast transformants that have only one codon-optimised gene. The strains show a considerably shorter lag phase and grow to their maximum optical density considerably faster (see example 2). The combination of three codon-optimised genes enables recombinant S. cerevisiae cells to convert L-arabinose considerably more efficiently.

The object is further solved according to the invention by the provision of expression cassettes comprising a nucleic acid molecule according to the invention.

Furthermore, the expression cassettes according to the invention preferably comprise promoter and terminator sequences.

Promoter sequences are preferably selected from HXT7, truncated HXT7, PFK1, FBA1, PGK1, ADH1 and TDH3.

Terminator sequences are preferably selected from CYC1, FBA1, PGK1, PFK1, ADH1 and TDH3.

Thereby, it is preferable that different pairs of promoter and terminator sequences control each of the three nucleic acid sequences. This is necessary to avoid possible homologous recombination between the promoter and/or terminator regions/sequences.

According to the invention, the pairs of promoter and terminator sequences are preferably selected from an HXT7 or truncated HXT7 promoter and CYC1 terminator, a PFK1 promoter and FBA1 terminator, and an FBA1 promoter and PGK1 terminator.

Particularly preferred is a nucleic acid sequence for araA controlled by the HXT7 or truncated HXT7 promoter and the CYC1 terminator.

Particularly preferred is a nucleic acid sequence for araB controlled by the PFK1 promoter and the FBA1 terminator.

Particularly preferred is a nucleic acid sequence for araD controlled by the FBA1 promoter and the PGK1 terminator.

For further details, see also example 3.

The expression cassettes according to the invention preferably comprise 5' and/or 3' recognition sequences as well.

Recognition sequences of the enzymes PacI and AscI are preferred.

The object is further solved according to the invention by provision of expression vectors, comprising a nucleic acid molecule or an expression cassette according to the invention.

The expression vectors according to the invention preferably comprise a selection marker as well.

The selection marker is preferably selected from a leucine marker, an uracil marker or a dominant antibiotic marker. A preferred dominant antibiotic marker is selected from geneticin, hygromycin and nourseothricin.

An expression vector according to the invention is preferably selected from the group p425H7synthAra, pRS303X, p3RS305X or p3RS306X.

For further details, see also example 3.

For industrial applications, it would be ideal if the microorganism used were capable of metabolising all of the sugars present in the medium. Since the yeasts that are currently used are not capable of metabolising the arabinose in the medium, it would be highly advantageous to provide the strains with this additional capability in stable manner. In order to achieve this, an expression vector with genes of an arabinose metabolic pathway is highly beneficial. This expression vector can then be genomically integrated in a stable manner and can allow for the metabolisation of arabinose in industrial strains.

This invention succeeded (see also Examples) in constructing a vector that codes for an expression cassette with three genes of an arabinose metabolic pathway, particularly a bacterial metabolic pathway. In this way, it is possible to circumvent the problems that may arise when several plasmids are present in the same cell at the same time ("Plasmid stress", Review of E. coli by Bailey (1993)). Furthermore, stable genomic integration of the arabinose metabolic pathway genes is enabled. The problems associated with constructing an expression cassette of the arabinose metabolic pathway genes and integrating it in a manner that is genomically stable have already been shown by Becker (2003) and Wiedemann (2005).

By selecting promoters and terminators in combination with using the improved L-arabinose isomerase and the codon-optimised versions of the genes involved, the construction of this functional expression cassette according to the invention was achieved.

The expression cassette constructed with the three genes according to the invention represents an excellent starting point for a direct genomic integration as well as enables subcloning into the integrative plasmids of the series pRS303X, pRS305X and pRS306X (Taxis and Knop, 2006).

Furthermore, a plurality of experimental obstacles and difficulties had to be overcome in the process of cloning the three genes with the different promoters and terminators, and these are reported in greater detail in the examples and figures.

Finding an L-arabinose isomerase that functions better, such as is more efficient, in yeast.

Cloning the isomerase proved to be difficult and time-consuming.

The vector according to the invention is the first vector described that contains all the essential genes for converting arabinose in yeast.

The vector contains all the genes in functional form and enables the recombinant yeast a good arabinose growth. Functionality as well as very good arabinose growth were by no means expected.

The object is further solved according to the invention by providing host cells that contain a nucleic acid molecule according to the invention, an expression cassette according to the invention, or an expression vector according to the invention.

In a particularly preferred embodiment, a nucleic acid molecule according to the invention, an expression cassette according to the invention or an expression vector according to the invention is integrated in stable manner in the genome of the host cell.

For industrial applications, it would be ideal if the microorganism used were capable of metabolising all of the sugars present in the medium. Since the yeasts that are currently used are not capable of metabolising the arabinose in the medium, it would be highly advantageous to provide the strains with this additional capability in stable manner. In order to achieve this, a nucleic acid molecule according to the invention, an expression cassette according to the invention or an expression vector according to the invention can be genomically integrated in stable manner and can allow for the metabolisation of arabinose in industrial strains. Using the nucleic acid molecules according to the invention ensures a very efficient arabinose conversion in industrial strains. Previously, the practice of introducing the genes of the bacterial L-arabinose metabolic pathway individually was associated with the difficulty that the genes were not present in an optimal ratio to each other. The transformations were time-consuming and the resulting arabinose metabolism was often not as efficient as desired. Moreover, the properties provided were often not stable. In contrast, the expression cassette according to the invention or the expression vector according to the invention, respectively, enable the bacterial L-arabinose metabolic pathway to be introduced quickly and functionally. With the selection of the promoters, it was possible to combine the genes together on one nucleic acid molecule, one expression cassette or one expression vector. The integration of the nucleic acid molecule according to the invention, the expression cassette according to the invention or the expression vector according to the invention, respectively, further guarantees an efficient arabinose conversion.

A host cell according to the invention is preferably a fungus cell, and more preferably a yeast cell, such as *Saccharomyces* species, *Kluyveromyces* sp., *Hansenula* sp., *Pichia* sp. or *Yarrowia* sp.

In particular, a host cell according to the invention is selected from BWY1, CEN.PK113-7D, Red Star Ethanol Red and Fermiol.

The object is further solved according to the invention by providing methods for producing bioethanol. One method according to the invention comprises the expression of a nucleic acid molecule according to the invention, an expression cassette according to the invention, or an expression vector according to the invention in a host cell.

Thereby, the method is preferably carried out in a host cell according to the invention.

The object is further solved according to the invention by the use of a nucleic acid molecule according to the invention, an expression cassette according to the invention, an expression vector according to the invention, or a host cell according to the invention to produce bioethanol.

The object is further solved according to the invention by the use of nucleic acid molecule according to the invention, an expression cassette according to the invention, an expression vector according to the invention, or a host cell according to the invention for recombinant fermentation of pentose-containing biomaterial.

For the methods and uses, see the examples and figures. The results of fermentation recorded in example 2 show that especially the codon-optimised genes of araA, araB and araD enable the yeast transformants to metabolise arabinose more efficiently. The result of this is faster conversion of the sugar and a significantly higher ethanol yield.

The object is further solved according to the invention by providing a polypeptide selected from the group of a. a polypeptide which is at least 70%, preferably at least 80% identical to the amino acid sequence that is coded by SEQ ID NO: 3, 4 or 5, and has an in vitro and/or in vivo pentose isomerase function, b. a naturally occurring variant of a polypeptide including the amino acid sequence that is coded by SEQ ID NO: 3, 4 or 5, which has an in vitro and/or in vivo pentose isomerase function, c. a polypeptide which is identical to the amino acid sequence that is coded by SEQ ID NO: 3, 4 or 5, and has an in vitro and/or in vivo pentose isomerase function, and d. a fragment of the polypeptide from a., b. or c., comprising a fragment of at least 100, 200 or 300 continuous amino acids of the amino acid sequence that is coded by SEQ ID NO: 3, 4 or 5.

Such a polypeptide is preferably selected from the group of a. a polypeptide which is at least 70%, preferably at least 80% identical to the amino acid sequence according to SEQ ID NO: 6 or 7, and has an in vitro and/or in vivo pentose isomerase function, b. a naturally occurring variant of a polypeptide comprising the amino acid sequence according to SEQ ID NO: 6 or 7, which has an in vitro and/or in vivo pentose isomerase function, c. a polypeptide which is identical to the amino acid sequence according to SEQ ID NO: 6 or 7, and has an in vitro and/or in vivo pentose isomerase function, and d. a fragment of the polypeptide from a., b. or c., comprising a fragment of at least 100, 200 or 300 continuous amino acids according to SEQ ID NO: 6 or 7.

A polypeptide according to the invention preferably comprises a polypeptide which is at least 90%, preferably 95% identical to the amino acid sequence that is coded by SEQ ID NO: 3, 4 or 5, and has an in vitro and/or in vivo pentose isomerase function.

Such a polypeptide according to the invention preferably comprises a polypeptide which is at least 90%, preferably 95% identical to the amino acid sequence according to SEQ ID NO: 6 or 7, and has an in vitro and/or in vivo pentose isomerase function.

The amino acid sequence with SEQ ID NO. 6 is the amino acid sequence of *Bacillus licheniformis* L-arabinose isomerase (araA). This amino acid sequence is preferably coded by the nucleic acid sequences with SEQ ID NOs. 3 or 4.

The amino acid sequence with SEQ ID NO. 7 is the amino acid sequence of *Clostridium acetobutylicum* L-arabinose isomerase (araA). This amino acid sequence is preferably coded by the nucleic acid sequence with SEQ ID NO. 5.

The pentose is arabinose, in particular L-arabinose.

The polypeptide according to the invention preferably originates from a bacterium, more preferably from *Bacillus licheniformis* or *Clostridium acetobutylicum*.

These L-arabinose isomerases are advantageous for the growth of yeast transformants on arabinose medium. A number of different experiments indicated that the L-arabinose isomerase from *B. subtilis* that was used previously represents a limiting step in the decomposition of arabinose in yeast (Becker and Boles, 2003; Wiedemann, 2003; Karhumaa et al, 2006; Sedlak and Ho, 2001). Example 1 shows (see also FIG. 4) that the growth of yeast transformants on arabinose medium is significantly improved particularly by the expression of L-arabinose isomerase from *C. acetobutylicum* and from *B. licheniformis*, in comparison to the isomerase from *B. subtilis*.

The object is further solved according to the invention by providing an isolated nucleic acid molecule that codes for a polypeptide according to the invention.

Additionally, the object is further solved according to the invention by providing a host cell that contains such an isolated nucleic acid molecule.

For preferred embodiments of the isolated nucleic acid molecule and of the host cells, reference is made to the embodiments described above.

The polypeptide according to the invention, the isolated nucleic acid molecule according to the invention and the host cell according to the invention are preferably used in the production of bioethanol and for recombinant fermentation of pentose-containing biomaterial.

A further aspect of the present invention are host cells that contain one or more modifications, such as nucleic acid molecules.

An additional modification of such kind is a host cell that overexpresses a TAL1 (transaldolase) gene, such as is described by the inventors in EP 1 499 708 B1, for example.

A further such additional modification is a host cell that contains a nucleic acid coding for a specific L-arabinose transporter gene (araT), particularly such as a specific L-arabinose transporter gene from the genome of *P. stipitis*, such as is described by the inventors in German Patent Application DE 10 1006 060 381.8, filed on Dec. 20, 2006.

Further biomass with significant amounts of arabinose (source of the data: U.S. Department of Energy:

| Type of biomass | L-arabinose [%] |
|---|---|
| Switchgrass | 3.66 |
| Large *bothriochloa* | 3.55 |
| Tall fescue | 3.19 |
| *Robinia* | 3 |
| Corn stover | 2.69 |
| Wheat straw | 2.35 |
| Sugar can bagasse | 2.06 |
| Chinese *lespedeza* | 1.75 |
| *Sorghum bicolor* | 1.65 |

The nucleic acids, expression cassettes, expression vectors and host cells according to the invention are also of great importance for their utilization.

Possible uses of the nucleic acids, expression cassettes, expression vectors and host cells according to the invention include both the production of bioethanol and the manufacture of high-quality precursor products for further chemical synthesis.

The following list originates from the study "Top Value Added Chemicals From Biomass". Here, 30 chemicals were categorized as being particularly valuable, which can be produced from biomass.

| Number of C atoms | Top 30 Candidates |
|---|---|
| 1 | hydrogen, carbon monoxide |
| 2 | |
| 3 | glycerol, 3-hydroxypropionic acid, lactic acid, malonic acid, propionic acid, serine |
| 4 | acetoin, asparaginic acid, fumaric acid, 3-hydroxybutyrolactone, malic acid, succinic acid, threonine |
| 5 | arabitol, furfural, glutamic acid, itaconic acid, levulinic acid, proline, xylitol, xylonic acid |
| 6 | aconitic acid, citrate, 2,5-furandicarboxylic acid, glucaric acid, lysine, levoglucosan, sorbitol |

It is important to have the nucleic acids, expression cassettes, expression vectors and host cells according to the invention available as soon as these chemicals are produced from lignocellulose by biokonversion (e.g. fermentations with yeasts).

The present invention will be explained in greater detail in the following figures, sequences and examples, without limitation thereto. The references cited are fully incorporated herein by reference thereto. In the sequences and figures are shown:

BRIEF DESCRIPTION OF THE SEQUENCES

SEQ ID NO: 1 shows the gene sequence of the open reading frame (ORF) of araB$^{mut}$ from *E. coli* in a codon-optimised form.

SEQ ID NO: 2 shows the gene sequence of the open reading frame (ORF) of araD from *E. coli* in a codon-optimised form.

SEQ ID NO: 3 shows the gene sequence of the open reading frame (ORF) of araA from *B. licheniformis* in a codon-optimised form.

SEQ ID NO: 4 shows the gene sequence of the open reading frame (ORF) of araA from *B. licheniformis*.

SEQ ID NO: 5 shows the gene sequence of the open reading frame (ORF) of araA from *C. acetobutylicum*.

SEQ ID NO: 6 shows the amino acid sequence of the *Bacillus licheniformis* L-arabinose isomerase (araA). This amino acid sequence is preferably coded by the nucleic acid sequences with SEQ ID NOs. 3 or 4.

SEQ ID NO: 7 shows the amino acid sequence of the *Clostridium acetobutylicum* L-arabinose isomerase (araA). This amino acid sequence is preferably coded by the nucleic acid sequence with SEQ ID NO. 5.

Biomass consists of cellulose, hemicellulose and lignin. The second most frequently occurring hemicellulose is a highly branched polymer consisting of pentoses, uronic acids and hexoses. The hemicellulose consists in a large proportion of the pentoses xylose and arabinose.

Figure 1:
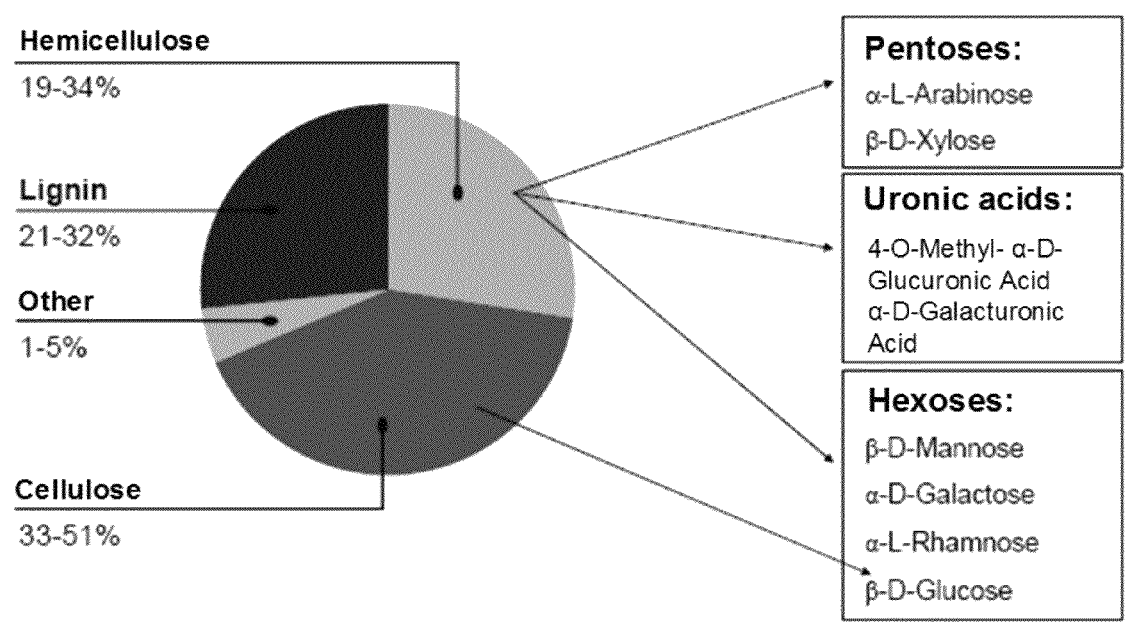
FIG. 1 Composition of the biomass.
Figure 2:
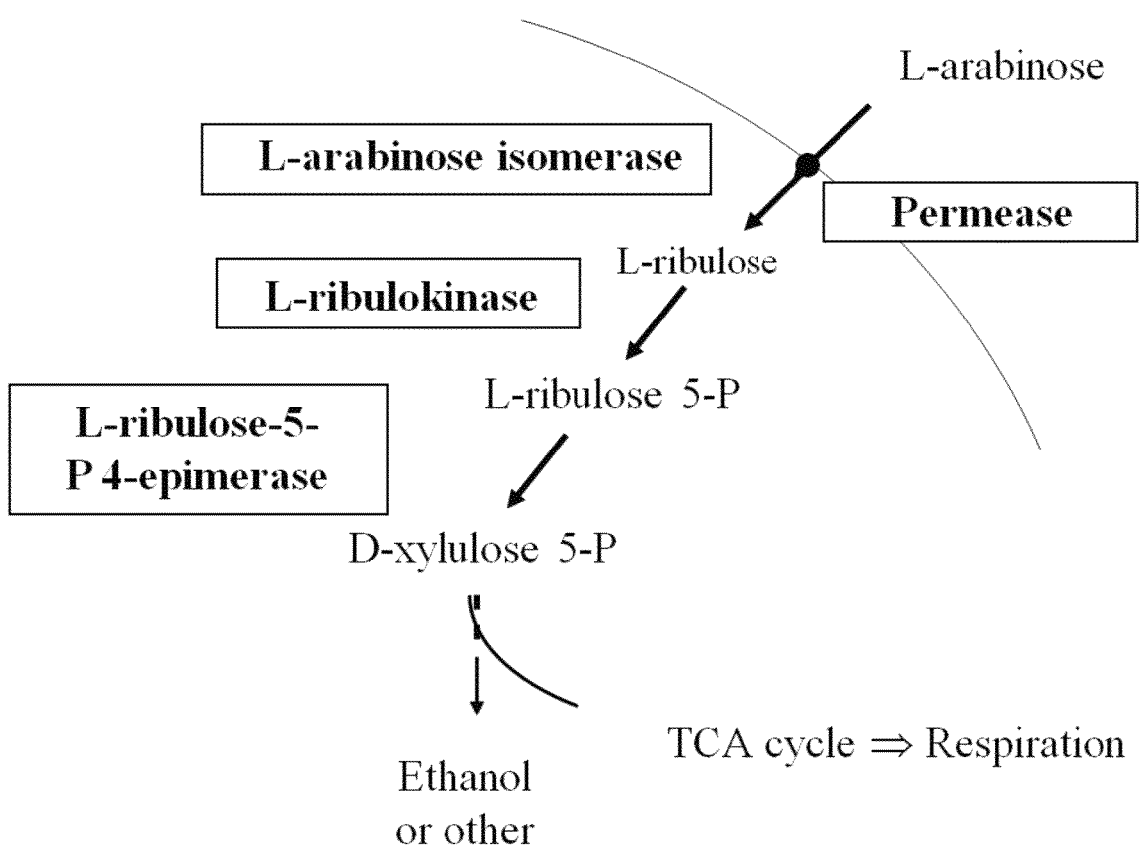

FIG. 2 Scheme of the metabolism of L-arabinose in recombinant *S. cerevisiae* by integration of a bacterial L-arabinose metabolic pathway.

Figure 3A:
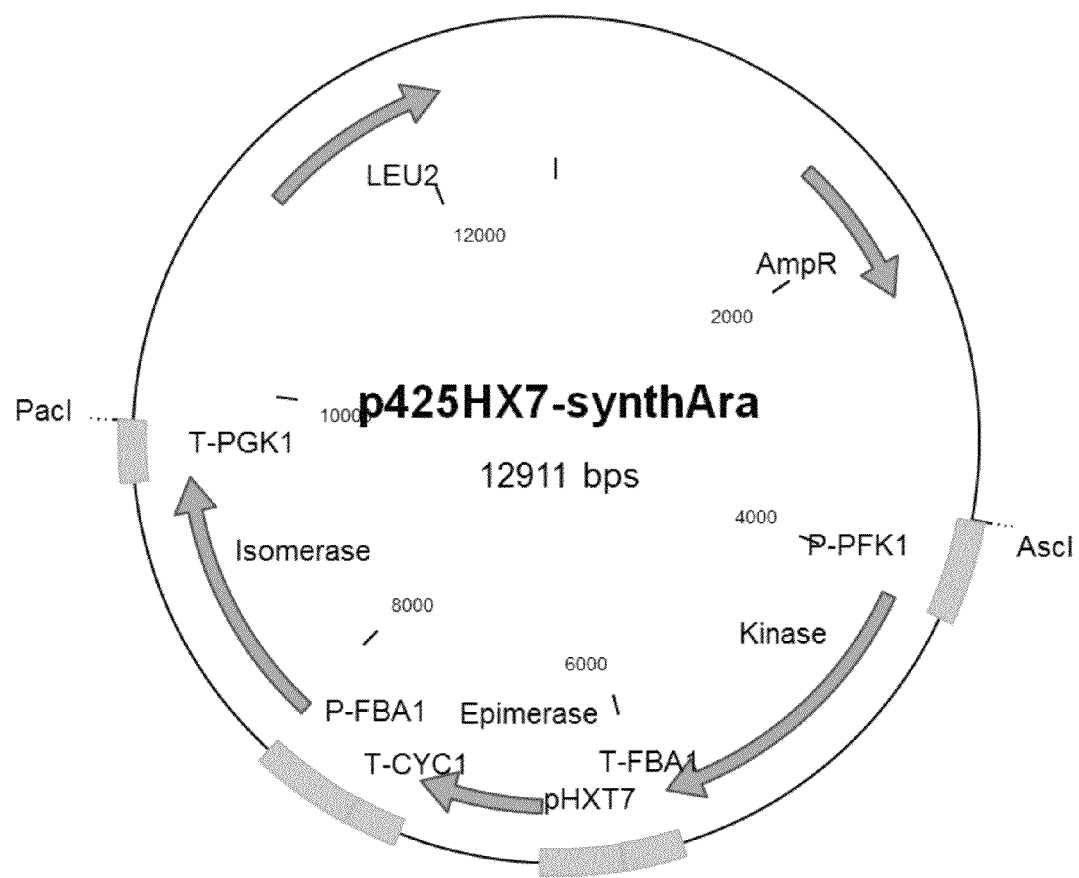
Figure 3B:
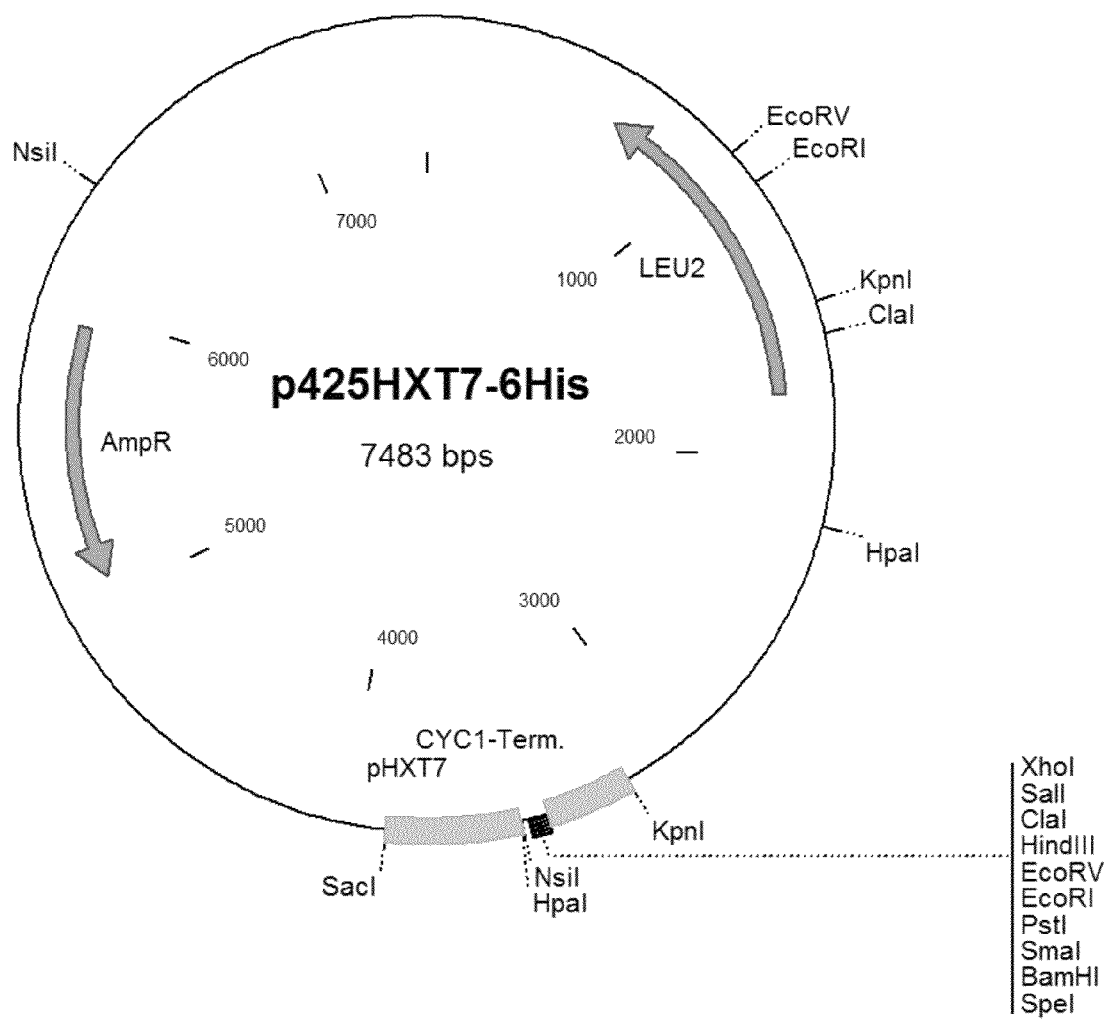

FIGS. 3A-3B Vectors used and their construction.

The initial plasmid for construction of the vector p425H7synthAra (FIG. 3 A) was the plasmid p425HXT7-6HIS (FIG. 3 B). The open reading frames of the codon-optimised genes of araA from *B. licheniformis* and araB$^{mut}$ and araD from *E. coli* were amplified and cloned into the plasmid p425HXT7-6HIS after various promoters and terminators. The primers were selected in such manner that the resulting expression cassette was flanked by the restriction sites of enzymes PacI and AscI. Thereby, the plasmid p425H7synthAra was produced, which has a leucine marker.

Figure 4:
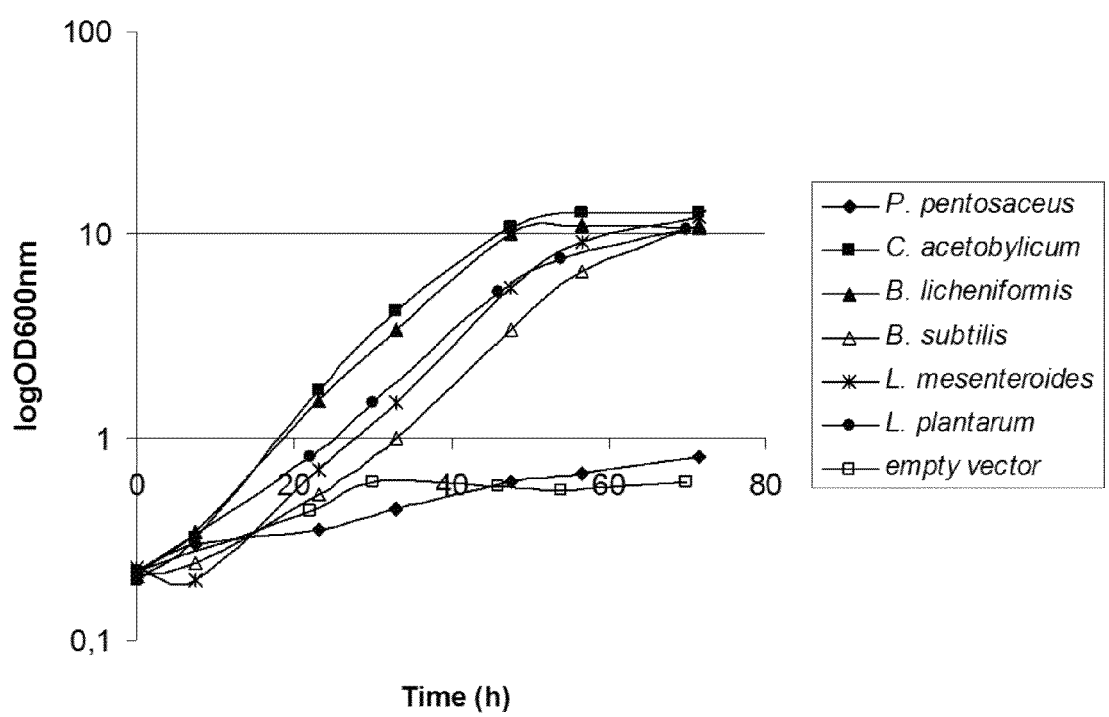

FIG. 4 Growth on arabinose using various L-arabinose isomerase genes.

Growth curves of recombinant *S. cerevisiae* strains containing the bacterial L-arabinose metabolism with various L-arabinose isomerases. Growth tests were conducted in 5 ml SM medium with 2% arabinose under aerobic conditions. The L-arabinose isomerases of *C. acetobutylicum, B. licheniformis, P. pentosaceus, L. plantarum* and *L. mesenteroides* were tested. The L-arabinose isomerase from *B. subtilis* and the empty vector p423HXT7-6HIS were used as controls.

Figure 5:
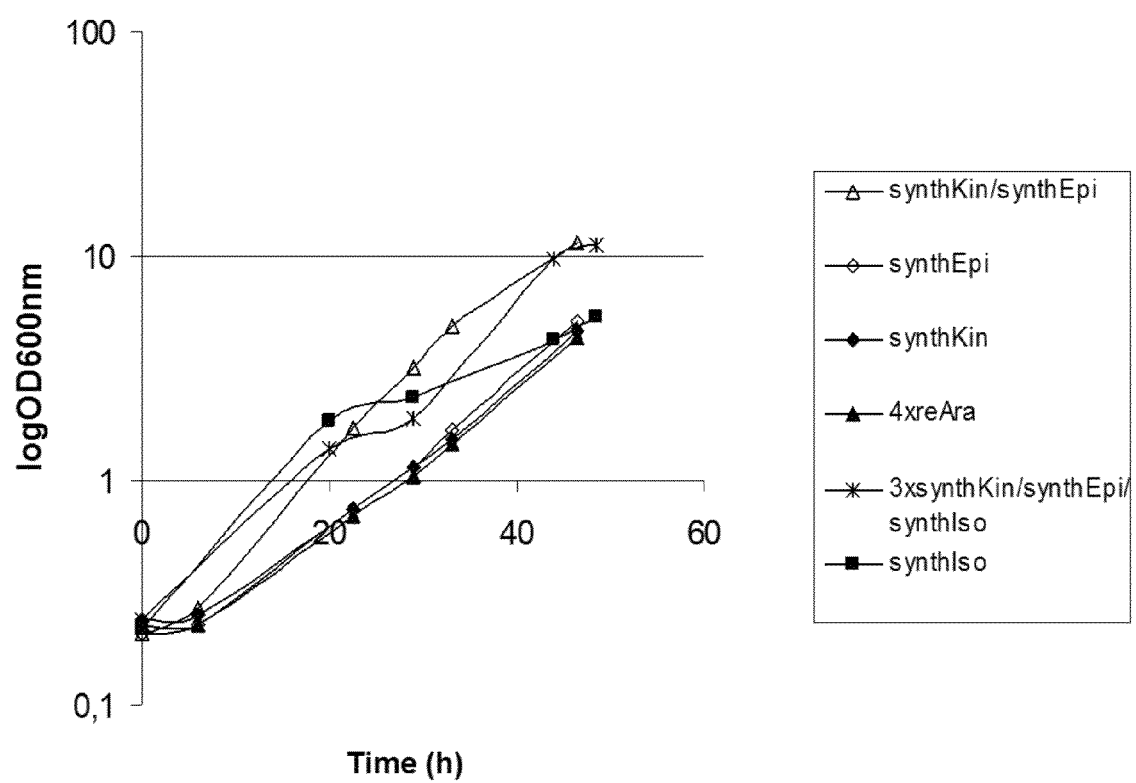

FIG. 5 Growth on arabinose using codon-optimised arabinose metabolic pathway genes.

Growth curves of recombinant *S. cerevisiae* strains containing the bacterial L-arabinose metabolism with different combinations of codon-optimised genes and the genes with original sequences. Growth tests were conducted in 5 ml SM medium with 2% arabinose under aerobic conditions. Each of the combinations that contained one of the codon optimised genes respectively, and the combination containing all three codon-optimised genes were tested. In addition, the combination in which the codon-optimised genes of kinase and epimerase were present was also tested. A recombinant yeast strain with the four genes having the original sequences was used as a control.

Figure 6A:
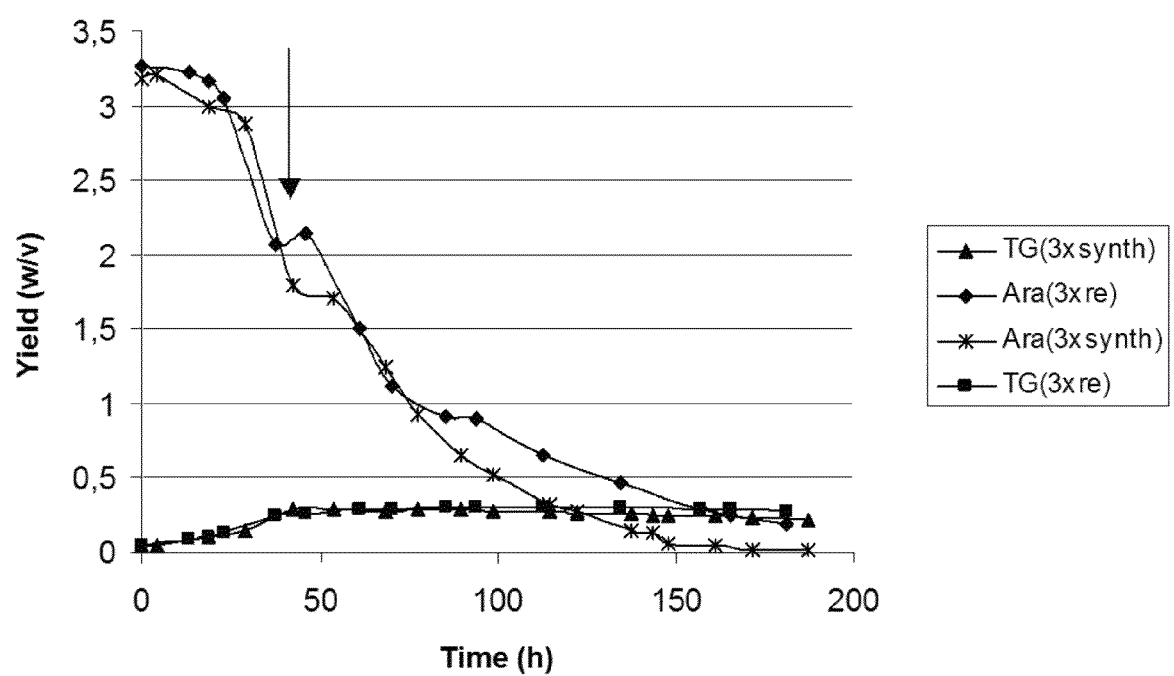
Figure 6B:
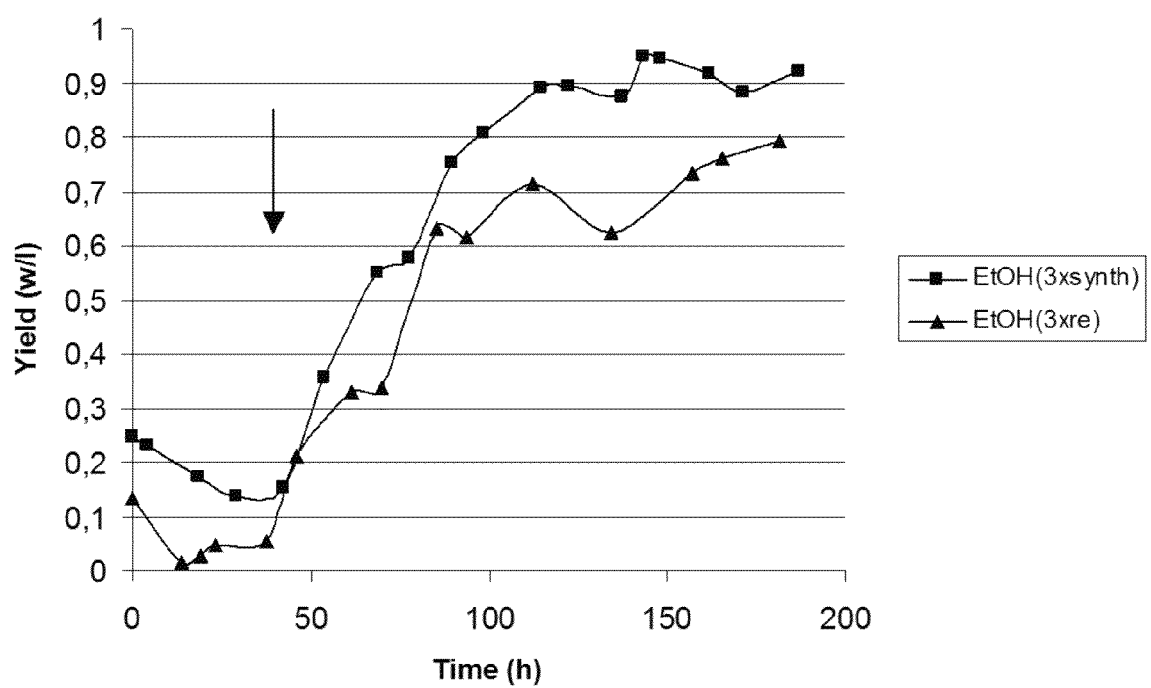

FIG. 6A-6B Ethanol formation using codon-optimised arabinose metabolic pathway genes.

The figure shows the results of HPLC analyses of the media supernatants from two fermentations. (6A) One fermentation was carried out with strain BWY1, which possesses plasmids p423H7synthIso, p424H7synthKin, p425H7synthEpi and pHL125$^{re}$ (3xsynth). (6B) In the other fermentation, strain BWY1 was tested, containing plasmids p423H7araABs$^{re}$, p424H7araB$^{re}$, p425H7araD$^{re}$ and pHL125$^{re}$ (3xre). The fermentations were carried out in SFM medium with 3% L-arabinose. The strains were grown to a high optical density in the fermenter.

Then, the fermentation was changed to anaerobic conditions (after 48 hours). The plots show arabinose consumption and ethanol production.

Figure 7:
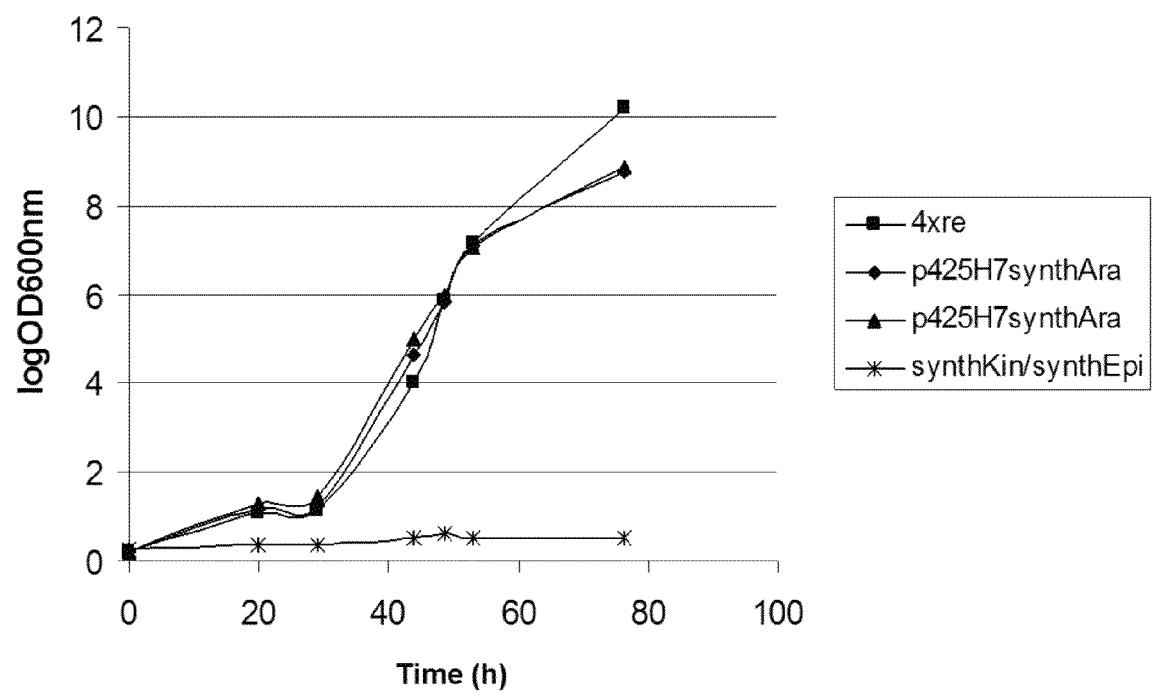

FIG. 7 Growth on arabinose using the constructed expression plasmid p425H7-synthAra.

Growth curves of recombinant S. cerevisiae strains containing bacterial L-arabinose metabolism in the form of the vector p425H7-synthAra. Growth tests were conducted in 5 ml SC medium with 2% arabinose under aerobic conditions. A recombinant yeast strain with the plasmids p423H7araABs$^{re}$, p424H7araB$^{re}$, p425H7araD$^{re}$ and pHL125$^{re}$, which had been tested in 5 ml SM medium with 2% arabinose, was used as the control.

EXAMPLE

Methods
1. Strains and Media
    Bacteria
    E. coli SURE (Stratagene)
    E. coli DH5α (Stratagene)
    Bacillus licheniformis (DSMZ)
    Clostridium acetobutylicum (DSMZ)
    Leuconostoc mesenteroides (DSMZ)
    Pediococcus pentosaceus (DSMZ)
    Lactobacillus plantarum (DSMZ)
    Full medium LB 1% Trypton, 0.5% yeast extract, 0.5% NaCl, pH 7.5 (see Maniatis, 1982). 40 µg/ml ampicillin was added to the medium after autoclaving for selection based on plasmid-coded antibiotic resistance. Solid culture media also contained 2% agar. Culturing was performed at 37° C.
    Yeast
    Strain BWY1:
    BWY1 is based on the strain JBY25 (MATa leu2-3,112 ura3-52 trp1-289 his3-Δ1MAL2-8c SUC2+ unknown mutations for better growth on arabinose); the strain JBY25 was selected further and possesses additional mutations for improved growth on L-arabinose under reduced oxygen conditions (Wiedemann, 2005)
    Synthetic Complete Selective Medium SC:
        0.67% yeast nitrogen base w/o amino acids, pH 6.3, amino acid/nucleobase solution, carbon source at the concentration indicated in each case
    Synthetic Minimal Selective Medium SM:
        0.16% yeast nitrogen base w/o amino acid and ammonium sulphate, 0.5% ammonium sulphate, 20 mM potassium dihydrogen phosphate, pH 6.3, carbon source at the concentration indicated in each case
    Synthetic Fermentation Medium (Mineral Medium) SFM: (Verduyn et al., 1992), pH 5.5
        Salts: $(NH_4)_2SO_4$, 5 g/l; $KH_2PO_4$, 3 g/l; $MgSO_4*7H_2O$, 0.5 g/l
        Trace elements: EDTA, 15 mg/l, $ZnSO_4*4.5$ mg/l; $MnCl_2*4H_2O$, 0.1 mg/l;
        $CoCl_2*6H_2O$, 0.3 mg/l; $CuSO_4$, 0.192 mg/l; $Na_2MoO_4*2H_2O$, 0.4 mg/l;
        $CaCl_2*2H_2O$, 4.5 mg/l; $FeSO_4*7H_2O$, 3 mg/l; $H_3BO_3$, 1 mg/l; KI, 0.1 mg/l
        Vitamins: Biotin, 0.05 mg/l; p-aminobenzoic acid, 0.2 mg/l; nicotinic acid, 1 mg/l;
        Calcium pantothenate, 1 mg/l; pyridoxin-HCL, 1 mg/l; thiamin-HCL, 1 mg/l;
        M inositol, 25 mg/l
        Concentration of amino acids and nucleobases in the synthetic complete medium (based on Zimmermann, 1975): Adenine (0.08 mM), arginine (0.22 mM), histidine (0.25 mM), isoleucine (0.44 mM), leucine (0.44 mM), lysine (0.35 mM), methionine (0.26 mM), phenylalanine (0.29 mM), tryptophan (0.19 mM), threonine (0.48 mM), tyrosine (0.34 mM), uracil (0.44 mM), valine (0.49 mM). L-arabinose and D-glucose were used as the carbon source.

Solid full and selective media also contained 1.8% agar. The yeast cells were cultured at 30° C. The synthetic mineral medium used for the fermentations contained salts, trace metals and vitamins in the concentrations listed above and L-arabinose as the carbon source. Stock solutions of the trace metals and of the vitamins were prepared. Both solutions were sterile filtered. Both were stored at 4° C. The pH value are critically important to the preparation of the trace metal solution. The various trace elements had to be completely dissolved in water one after the other in the order given above. After each addition, the pH value had to be adjusted to 6.0 with KOH before the next trace element could be added. Finally, the pH value was adjusted to 4.0 with HCl. 200 µl antifoaming agent (Antifoam2004, Sigma) was added to the medium to prevent foaming. Since the tests were carried out under anaerobic conditions, 2.5 ml/l of a Tween80-Ergosterol solution had to be added to the medium after autoclaving. This consists of 16.8 g Tween80 and 0.4 g Ergosterol, which was filled to 50 ml with ethanol and dissolved therein. The solution was sterile filtered. The salts and the antifoaming agent were autoclaved together with the complete fermenter. The arabinose was autoclaved separately from the rest of the medium. After the medium cooled down, the trace elements and vitamins were added to it.

2. Plasmids

| Plasmid | Source/Reference | Description |
| --- | --- | --- |
| p423HXT7-6HIS (=p423H7) | Becker and Boles, 2003 | 2µ expression plasmid for overexpression of various genes and for fusing the E. coli L-arabinose isomerase with an His$_6$ epitope; HIS3 selection marker gene, shortened HXT7 promoter and CYC1 terminator (Hamacher et al., 2002) |
| p424HXT7-6HIS (=p424H7) | Becker and Boles, 2003 | 2µ expression plasmid for overexpression of various genes and for fusing the mutated and the wild type E. coli L-ribulokinase with an His$_6$ epitope; TRP1 selection marker gene, shortened HXT7 promoter and CYC1 terminator (Hamacher et al., 2002) |
| p425HXT7-6HIS (=p425H7) | Becker and Boles, 2003 | 2µ expression plasmid for overexpression of various genes; LEU2 selection marker gene, shortened HXT7 promoter and CYC1 terminator (Hamacher et al., 2002) |
| p426HXT7-6HIS (=p426H7) | Hamacher et al., 2002 | 2µ expression plasmid for overexpression of genes producing an His$_6$ epitope; URA3 selection marker gene, shortened HXT7 promotor and CYC1 terminator |

| Plasmid | Source/Reference | Description |
| --- | --- | --- |
| p423H7araABs$^{re}$ | Becker and Boles, 2003 | *B. subtilis* araA in p423HXT7-His, re-isolated from JBY25-4M |
| p424H7araB | Becker and Boles, 2003 | *E. coli* araB in p423HXT7-His |
| p424H7araB$^{re}$ | Becker and Boles, 2003 | *E. coli* araB in p423HXT7-His; re-isolated from JBY25-4M, mutation in araB, which enables arabinose growth |
| p425H7araD$^{re}$ | Becker and Boles, 2003 | *E. coli* araD in p425HXT7-His; re-isolated from JBY25-4M |
| p423H7-synthIso | | *B. licheniformis* araA codon-optimised in p423HXT7-His |
| p424H7-synthKin | | *E. coli* araB codon-optimised in p424HXT7-His, with mutation in araB |
| p425H7-synthEpi | | *E. coli* araD codon-optimised in p425HXT7-His |
| p425H7-synthAra | | 2µ plasmid with codon-optimised genes araA, araB$^{mut}$ and araD; araA under control of the FBA1 promoter and PGK1 terminator, araB$^{mut}$ under control of the PFK1 promoter and FBA1 terminator, and araD under control of the shortened HXT7 promoter and the CYC1 terminator, LEU2 selection marker gene |
| pHL125$^{re}$ | Liang and Gaber, 1996 | 2µ plasmid with the GAL2 gene expressed after the ADH1 promoter, URA3 selection marker gene; re-isolated from JBY25-4M |

3. Transformation:

Transformation of *E. coli*

The *E. coli* cells were transformed by the electroporation method described by Dower et al. (1988) and Wirth (1993) using an Easyject prima device (EQUIBO).

Transformation of *S. cerevisiae*

*S. cerevisiae* strains were transformed with plasmid DNA or DNA fragments using the lithium acetate method of Gietz and Woods (1994).

4. Preparation of DNA

Isolation of Plasmid DNA from *E. coli*

Plasmid DNA was isolated from *E. coli* with the alkaline lysis procedure developed by Birnboim and Doly (1979), modified according to Maniatis et al. (1982), or alternatively with the "QIAprep Spin Miniprep Kit" manufactured by Qiagen.

Highly pure plasmid DNA for sequencing was prepared with the "Plasmid Mini Kit" manufactured by Qiagen according to the manufacturer's instructions.

Isolation of Plasmid DNA from *S. cerevisiae*

The cells of a stationary yeast culture (5 ml) were harvested by centrifuging, washed and resuspended in 400 µl P1 buffer (Plasmid Mini Kit, Qiagen). After the addition of 400 µl P2 buffer and ⅔ volume glass beads (Ø0.45 mm, cell disruption was performed by shaking for 5 minutes on a Vibrax (Vibrax-VXR manufactured by Janke & Kunkel or IKA). The residue was filled with ½ volume P3 buffer, mixed and incubated on ice for 10 min. After centrifuging for 10 minutes at 13000 rpm, the plasmid DNA was precipitated at room temperature by adding 0.75 ml isopropanol to the residue. The DNA was pelletized by centrifuging at 13000 rpm for 30 min. and washed with 70% ethanol, dried and resuspended in 20 µl water. 1 µl of the DNA was used for the transformation in *E. coli*.

Determination of DNA Concentration

The DNA concentration was measured by spectrophotometry in a wavelength range of 240-300 nm. If the purity of the DNA, as determined by the quotient $E_{260nm}/E_{280nm}$, is 1.8, extinction $E_{260nm}=1.0$ corresponds to a DNA concentration of 50 µg dsDNA/ml (Maniatis et al., 1982).

DNA Amplification Using PCR

Use of the Phusion™ High Fidelity System

The polymerase chain reaction was carried out in a total volume of 50 µl with the "Phusion™ High Fidelity PCR System" manufactured by the company Finnzymes in accordance with the manufacturer's instructions. Each stock solution consisted of 1-10 ng DNA or 1-2 yeast colonies as a synthesis model, 0.2 mM dNTP-Mix, 1× buffer 2 (contains 1.5 mM MgCl$_2$), 1 U polymerase, and 100 pmol of each of the corresponding oligonucleotide primers. The PCR reaction was carried out in a thermocycler manufactured by the company Techne and the following PCR conditions were selected according to requirements:

| | | |
| --- | --- | --- |
| 1. 1× | 30 sec, 98° C. | Denaturation of DNA |
| 2. 30× | 10 sec, 98° C. | Denaturation of DNA |
| | 30 sec, 56-62° C. | Annealing/binding of oligonucleotides to the DNA |
| | 0.5-1 min, 72° C. | DNA synthesis/elongation |
| 3. 1× | 7 min, 72° C. | DNA synthesis/elongation |

The polymerase was added after the first denaturation step ("hot start PCR"). The number of synthesis steps, the annealing temperature and the elongation time were adapted to the specific melting temperatures of the oligonucleotides used and the size of the expected product. The PCR products were tested with agarose gel electrophoresis and then cleaned up.

DNA Purification of PCR Products

The PCR products were purified with the "QIAquick PCR Purification Kit" manufactured by Qiagen in accordance with the instructions of the manufacturer.

Gel Electrophoretic Separation of DNA Fragments

DNA fragments having a size of 0.15-20 kb were separated in 0.5-1% agarose gels with 0.5 µg/ml ethidium bromide. 1×TAE buffer (40 mM Tris, 40 mM acetic acid, 2 mM EDTA) was used as the gel and running buffer (Maniatis et al., 1982). A lambda phage DNA digested with the restriction endonucleases EcoRI and HindIII was used as the size standard. Before loading, 1/10 volume blue marker (1×TAE buffer, 10% glycerin, 0.004% bromophenol blue) was added to the DNA samples, which were rendered visible after separation by irradiation with UV light (254 nm).

Isolation of DNA Fragments from Agarose Gels

The desired DNA fragment was cut out of the TAE agarose gel under long-wave UV light (366 nm) and isolated with the "QIAquick Gel Extraction Kit" manufactured by Qiagen in accordance with the manufacturer's instructions.

5. Enzymatic Modification of DNA
DNA Restriction

Sequence-specific cleaving of the DNA with restriction endonucleases was conducted for 1 hour with 2-5 U enzyme per µg DNA under the incubation conditions recommended by the manufacturer.

Example 1

Screen for Better L-arabinose Isomerases

A) Performance of the Screen

Several experiments indicated that the L-arabinose isomerase from *B. subtilis* represents a limiting step in the breakdown of arabinose in yeast (Becker and Boles, 2003; Wiedemann, 2003; Karhumaa et al, 2006; Sedlak and Ho, 2001). In order to improve the arabinose metabolic path, five L-arabinose isomerases from different organisms were tested.

For this, genomic DNA was isolated from the organisms *C. acetobutylicum*, *B. licheniformis*, *P. pentosaceus*, *L. plantarum* and *L. mesenteroides* (see "Isolation of plasmid DNA from *S. cerevisiae*"). The cells were cultivated, harvested and absorbed in the buffer. Cell disruption was effected using glass beads. Then, the DNA was precipitated, washed, and used for the PCR. The open reading frame (ORF) of araA from the organisms listed was amplified with primers, which also had homologous areas to the HXT7 promoter and CYC1 terminator. The PCR products obtained were transformed in yeast together with the EcoRI/BamHI linearised vector p423HXT7-6His and cloned by in vivo recombination into the plasmid between the HXT7 promoter and CYC1 terminator. The sequence of the plasmids obtained was verified by restriction analysis. The functionality of the new isomerases and their effect on the arabinose metabolism also needed to be studied.

For this purpose, recombinant yeast strains were produced, containing one of the new isomerases and the rest of the bacterial arabinose metabolic pathway genes (p424H7araB$^{re}$, p425H7araD$^{re}$ and pHL125$^{re}$).

B) Growth Behaviour

Growth of the strains was tested under aerobic conditions in a medium containing arabinose. The recombinant yeast strain containing the isomerase from *B. subtilis* was used as the control. A yeast strain with the empty vector p423HXT7-6HIS was constructed as the negative control.

The strains with the various isomerase plasmids were cultured in SM medium with 2% arabinose and inoculated with a $OD_{600nm}=0.2$ in 5 ml SM medium with 2% arabinose. This was incubated in test tubes on a shaking flask under aerobic conditions at 30° C. Samples were taken regularly to determine optical density.

The results are shown in FIG. 4. It was shown that, compared with the isomerase from *B. subtilis*, particularly the expression of L-arabinose isomerase from *C. acetobutylicum* and from *B. licheniformis* significantly improved the growth of yeast transformants on arabinose medium.

Example 2

Codon-Optimisation of Genes for Arabinose Decomposition in Yeast

A) Codon-Optimisation of Genes According to the Codon Usage of the Glycolysis Genes from *S. cerevisiae*

The preferred codon usage of the glycolysis genes from *S. cerevisiae* was calculated and is listed in table 1. The ORF of genes araA and araB$^{mut}$ from *E. coli* were codon-optimised as well as the ORF of the gene araA from *B. licheniformis*. This means, the sequences of the open reading frames were adapted to the preferred codon usage listed below. The protein sequence of the enzymes remained unchanged. The genes were synthesised at the facilities of an independent company delivered in dried form in company owned house vectors.

More detailed information about gene synthesis is available.

TABLE 1

Preferred codon usage of glycolysis genes from *S. cerevisiae*.

| Amino acid | preferred codon |
|---|---|
| Ala | GCT |
| Arg | AGA |
| Asn | AAC |
| Asp | GAC, (GAT) |
| Cys | TGT |
| Gln | CAA |
| Glu | GAA |
| Gly | GGT |
| His | CAC |
| Ile | ATT, (ATC) |
| Leu | TTG |
| Lys | AAG |
| Met | ATG |
| Phe | TTC |
| Pro | CCA |
| Ser | TCT, (TCC) |
| Thr | ACC, (ACT) |
| Trp | TGG |
| Tyr | TAC |
| Val | GTT, (GTC) |
| Stop | TAA |

B) Introduction of Codon-Optimised Genes into the BWY1 Strain

In order to transform the three codon-optimised genes into the BWY1 strain and test them, the genes had to be subcloned in yeast vectors. For this purpose, the codon-optimised araA ORF, the araB$^{mut}$ ORF and the araD ORF were amplified with primers, so that homologous overhangs to the shortened HXT7 promoter and the CYC1 terminator were created. The 2µ expression plasmids p423HXT7-6HIS, p424HXT7-6HIS, p425HXT7-6HIS were linearised with restriction endonucleases in the range between the HXT7 promoter and the CYC1 terminator. The PCR product from araA was transformed in yeast with the linearised p423HXT7-6HIS and cloned to the plasmid p423H7-synthIso by in vivo recombination. The same procedure was followed with the PCR product araB$^{mut}$ and the linearised vector p424HXT7-6HIS. This produced the plasmid p424H7synthKin. Plasmid p425H7- synthIso was produced by in vivo recombination of PCR product araD and the linearised vector p425HXT7-6HIS in yeast. The plasmids were isolated from the yeast and amplified in E. coli. After the plasmids were isolated from E. coli, the plasmids were examined by restriction analysis. One of each of the plasmids with the codon-optimised genes was transformed into the yeast strain BWY1 together with the three original, re-isolated plasmids, to test for functionality and for further analysis, so that all of the recombinant strains produced contained a complete arabinose metabolic pathway. In addition, the combination p424H7synthKin and p42457synthEpi was tested with the original, re-isolated plasmids as well as a batch in which the yeast transformant possessed all three new plasmids. The transformation with the four plasmids in each case took place at the same time. The transformants were plated on SM medium with 2% glucose. After two days, the colonies obtained were streaked out onto SM medium with 2% arabinose. A yeast strain that contained the four original, re-isolated plasmids was used as a positive control.

C) Growth Behaviour

The growth of the strain BWY1 with the various plasmid combinations of codon-optimised genes and original genes was examined in growth tests on arabinose-containing medium under aerobic conditions.

The strains with the various plasmid combinations were cultured in SM medium with 2% L-arabinose and inoculated with an $OD_{600nm}$=0.2 in 5 ml SM medium with 2% L-arabinose. Incubation took place in test tubes under aerobic conditions at 30° C. Samples were taken regularly to determine optical density.

The results of the aerobic growth curve are shown in FIG. 5. It can be seen clearly that recombinant yeast strains that possess only one of the optimised genes show little or no growth advantages compared to the strain with the four original plasmids in a medium containing arabinose. However, yeast transformants with the two optimised genes of kinase and epimerase and yeast transformants with three optimised genes showed a clear growth advantage in a medium containing arabinose. The strains manifested a significantly shorter lag phase and grew to their maximum optical density considerably more quickly.

This shows that the combination of the three codon-optimised genes enables recombinant S. cerevisiae cells to convert L-arabinose significantly more efficiently.

D) Ethanol Production

FIGS. 6 (A) and (B) shows the results of HPLC analyses of two fermentations. One recombinant yeast strain contains plasmids p423H7synthIso, p424H7synthKin, p425H7synthEpi and pHL125$^{re}$, the other contains plasmids p423H7araABs$^{re}$, p424H7araB$^{re}$, p425H7araD$^{re}$ and pHL125$^{re}$. The fermentations were conducted in SFM medium with 3% L-arabinose. FIG. 6 (A) shows the arabinose consumption and the dry weight of both strains. FIG. 6 (B) illustrates the ethanol production of the two strains.

The strains were cultivated in the fermenter aerobically until they reached a dry weight of approx. 2.8 g/l. When sufficient cell mass was present, the fermentations were switched to anaerobic conditions. The figure shows the plots of arabinose metabolism and ethanol production. The byproducts produced, arabitol, acetate and glycerin, have not been listed because they were produced in comparable quantities by both strains.

As the plots show, ethanol production begins immediately after the switch to anaerobic conditions for both strains (the switch to anaerobic conditions is shown in FIGS. 6 (A) and (B) by an arrow). The ethanol that was already present in the medium at the start of the fermentation was not produced by the yeasts, it originated from the Tween80/Ergosterol solution. Under the aerobic conditions that prevailed in the beginning, ethanol was decomposed by yeast by respiration.

After about 80 hours, the strain that has the arabinose metabolic pathway genes in codon-optimised form demonstrates significantly improved arabinose metabolism and increased ethanol production. The arabinose present in the medium has been completely consumed after just 150 hours. In contrast, even after 180 hours there is still arabinose in the medium with the strain with the original, reisolated plasmids.

The fermentation results show that the codon-optimised genes enable the yeast transformants to metabolise arabinose more efficiently. The result of this is that the sugar is metabolised faster and a significantly higher ethanol yield is obtained.

Example 3

Construction of an Expression Cassette with Three Genes for the Arabinose Metabolic Pathway The vector with the expression cassette with three genes for the arabinose metabolic pathway was constructed both to circument the problems that can arise when several plasmids are present in the same cell at the same time ("Plasmid stress", Review of E. coli by Bailey (1993)), and to enable stable genomic integration of the arabinose metabolic pathway genes. The issues associated with constructing an expression cassette of the arabinose metabolic pathway genes and integrating it individually in a manner that is genomically stable have already been shown by Becker (2003) and Wiedemann (2005). The expression cassette with the three genes that has now been constructed represents an excellent starting point for direct genomic integration and enables subcloning into the integrative plasmids of the series pRS303X, pRS305X und pRS306X (Taxis und Knop, 2006).

A) Construction of the Expression Cassette

The starting point for constructing the expression cassette was the plasmid p425H7-synthEpi, in which the codon-optimised form of epimerase was expressed from E. coli behind the shortened HXT7 promoter and in front of the CYC1 terminator. In order to prevent possible homologous recombination between identical promoter or terminator regions, the codon-optimised araB$^{mut}$-ORF must be expressed from E. coli between the PFK1 promoter and the FBA1 terminator, the codon-optimised araA-ORF from B. licheniformis between the FBA1 promoter and the PGK1 terminator. The plasmid p425H7-synthEpi was opened before the HXT7 promoter with restriction endonuclease SacI, streaked on an agarose gel, and eluted from the gel. The araB$^{mut}$ ORF was amplified by PCR. The PFK1 promoter and FBA1 terminator were amplified from genomic DNA of S. cerevisiae, the primers having been selected so that a 500 bp long sequence of the promoter and a 300 bp long sequence of the terminator were synthesised and homologous overhangs to the plasmid p425H7-synthEpi and to the araB$^{mut}$ ORF were produced at the same time. The primer that amplified the PFK1 promoter with the homologous regions to p425H7-synthEpi also contained a sequence for a PacI restriction site. The three PCR products were transformed in yeast together with the linearised vector and cloned into the plasmid via in vivo recombination. Restriction analysis was used to verify that the p425H7synthEpisynthKin plasmid produced had been successfully reconstructed. The functionality of the vector was tested. To do this, yeast transformants that contained the plasmids p425H7synthEpisynthKin and p423H7araABs$^{re}$ were prepared. The transformants were tested for arabinose growth. The strain was capable of growing on a medium containing arabinose. A yeast strain containing the vectors p424H7synthEpi and p423HXT7-6HIS was used as the negative control. This strain was not able to grow on the medium.

In the next step, the codon-optimised form of the isomerase from *B. licheniformis* was integrated into the vector. For this, plasmid p425H7synthEpisynthKin was linearised with NgoMVI after the CYC1 terminator, streaked onto an agarose gel and eluted from the gel. A 500 bp long sequence of the FBA1 promoter was amplified from genomic DNA of *S. cerevisiae*, and the primers were selected so that homologous overhangs to plasmid p425H7synthEpisynthKin in the CYC1 terminator and to the ORF of the codon-optimised araA were produced. A 300 bp long sequence of the PGK1 terminator was also amplified from genomic DNA of *S. cerevisiae*, in which a primer had overhangs to the ORF of the codon-optimised araA and the other primer included homologous overhangs to plasmid p425H7synthEpisynthKin and an AscI restriction site.

Restriction analysis was again used to verify the successful construction of the plasmid p425H7synthAra, and its functionality was tested. The test for functionality was performed for arabinose growth. Yeast transformants that contained the plasmid p425H7synthAra demonstrated growth on a medium containing arabinose. Growth curves in 5 ml SC medium with 2% arabinose were recorded. FIG. 7 shows that the transformants with vector p425H7synthAra demonstrate growth comparable to a strain with the four original, re-isolated plasmids.

B) Role of Promoters and Terminators

In order to avoid possible homologous recombination between the promoter and terminator regions, the three genes were cloned behind different promoters and terminators. In this context, the selection of the promoters was particularly important. It had been found in previous research (Becker and Boles, 2003) that the gene dose of the three genes relative to each other was critically important. In addition, all genes were to be strongly expressed. For these reasons, the decision was made to use the shortened HXT7 promoter, which is expressed strongly and constitutively, and the promoters PFK1 and FBA1, which are both known to promote strong expression of genes.

C) Examples of Vectors for the Expression Cassette

The starter plasmid for the construction of p425H7synthAra was the plasmid p425H7synthEpi, which is based on the plasmid p425HXT7-6HIS. The vector is a 2µ expression plasmid that possesses a leucine marker.

The three arabinose metabolic pathway genes were cloned into a vector one after the other under the control of various promoters and terminators. The expression cassette is flanked by the recognition sequences of the enzymes PacI and AscI.

Other possible expression vectors are come from the series pRS303X, p3RS305X and p3RS306X. These are integrative vectors that have a dominant antibiotic marker. More information about these vectors is provided in Taxis and Knop (2006).

REFERENCES

Becker, J. (2003)
Konstruktion und Charakterisierung eines L-Arabinose fermentierenden *Saccharomyces cerevisiae* Hefestammes.
Thesis, Heinrich-Heine-Universität Düsseldorf
Becker, J. und Boles, E. (2003)
A modified *Saccharomyces cerevisiae* strain that consumes L-arabinose and produces ethanol.
*Appl. Environ. Microbiol.* 69:4144-4150
Bailey, J. E. (1993)
Host-vector interactions in *Escherichia coli*.
*Adv. Biochem Eng.* 48.29-52
Bennetzen, J. L. und Hall, B. D. (1982)
Codon selection in yeast.
*J Biol Chem.* 257(6):3026-2031.
Birnboim, H. C. und J. Doly (1979)
A rapid alkaline extraction procedure for screening recombinant plasmid DNA.
*Nucl. Acids Res.* 7: 1513-1523
Dower, W. J., Miller, J. F. und Ragsdale, C. W. (1988)
High efficiency transformation of *E. coli* by high voltage electroporation.
*Nucl. Acids Res.* 16: 6127-6145
Gietz, R. D. und Woods, R. A. (1994)
High efficiency transformation in yeast.
In: Molecular Genetics of Yeast: Practical Approaches, J. A. Johnston (Ed.).
Oxford University Press pp. 121-134
Hamacher, T., Becker, J., Gárdonyi, M., Hahn-Hägerdal, B. und Boles., E. (2002)
Characterization of the xylose-transporting properties of yeast hexose transportes and their influence on xylose utilization.
*Microbiology* 148:2783-2788.
Hoekema A, Kastelein R A, Vasser M, de Boer H A. (1987)
Codon replacement in the PGK1 gene of *Saccharomyces cerevisiae*: experimental approach to study the role of biased codon usage in gene expression.
*Mol Cell Biol.* 7(8):2914-2924.
Karhumaa, K., Wiedemann, B., Hahn-Hägerdal, B., Boles, E. and Gorwa-Grauslund, M F. (2006)
Co-utilisation of L-arabinose and D-xylose by laboratory and industrial *Saccharomyces cerevisiae* strains.
*Microbial Cell Factories* 5(1):18
Maniatis T, Fritsch, E. F und Sambrook, J. (1982)
Molecular cloning. A laboratory manual.
Cold Spring Harbor Laboratory, New York.
Sedlak, M. und Ho, N. W. Y. (2001)
Expression of *E. coli* araBAD operon encoding enzymes for metabolizing L-arabinose in *Saccharomyces cerevisiae*.
*Enz. Microbiol.* 28:16-24
Taxis, C. und Knop, M. (2006)
System of centromeric, episomal, and integrative vectors based on drug resistance markers for *Saccharomyces cerevisiae*.
Bio Techniques 40, No. 1
Verduyn, C., Postma, E., Scheffers, W. A. und Van Dijken, J. P. (1992)
Effect of benzoic acid on metabolic fluxes in yeasts: a continuous-culture study on the regulation of respiration and alcoholic fermentation.
*Yeast* 8 (7), 501-17
Wiedemann, B. (2005)
Molekulargenetische und physiologische Charakterisierung eines rekombinanten Pentose-vergärenden Hefestammes. Diplomarbeit. Johann Wolfgang Goethe-Universität, Frankfurt am Main.
Wirth; R. (1993)
Elektroporation: Eine alternative Methode zur Transformation von Bakterien mit Plasmid-DNA. *Forum Mikrobiologie* 11 (507-515).
Wu G, Bashir-Bello N, Freeland S J. (2006)

The Synthetic Gene Designer: a flexible web platform to explore sequence manipulation for heterologous expression.
*Protein Expr Purif.* 47(2):441-445.

Zimmermann, F. K. (1975)
Procedures used in the induction of mitotic recombination and mutation in the yeast *Saccharomyces cerevisiae*.
*Mutation Res.* 31:71-81

We claim:

1. A host cell containing a nucleic acid molecule, which is operably linked to a heterologous promoter, and which encodes a polypeptide comprising SEQ ID NO: 7 or an amino acid sequence that is at least 90% identical to SEQ ID NO: 7; wherein the polypeptide has an in vitro and/or in vivo pentose isomerase function; and wherein the host cell is a *Saccharomyces cerevisiae* cell.

2. The host cell of claim 1, wherein the nucleic acid molecule encodes a polypeptide that is at least 95% identical to SEQ ID NO: 7 and has an in vitro and/or in vivo pentose isomerase function.

3. The host cell of claim 1, wherein the pentose is L-arabinose.

4. The host cell of claim 1, wherein the polypeptide originates from a bacterium.

5. The host cell of claim 4, wherein the polypeptide originates from *Clostridium acetobutylicum*.

6. The host cell, according to claim 1, wherein said polypeptide has SEQ ID NO: 7.

7. The host cell, according to claim 1, wherein the heterologous promoter is selected from the group consisting of the promoters of HXT7, PFK1, FBA1, PGK1, ADH1, TDH3 and a truncated promoter version of HXT7.

8. The host cell of claim 2, wherein the pentose is L-arabinose.

9. The host cell of claim 2, wherein the polypeptide originates from a bacterium.

10. The host cell of claim 9, wherein the polypeptide originates from *Clostridium acetobutylicum*.

11. The host cell, according to claim 2, wherein the heterologous promoter is selected from the group consisting of the promoters of HXT7, PFK1, FBA1, PGK1, ADH1, TDH3 and a truncated promoter version of HXT7.

12. A host cell containing a nucleic acid molecule comprising SEQ ID NO: 5 operably linked to a heterologous promoter, wherein the cell is a fungus cell.

13. The host cell of claim 12, which is a yeast cell.

14. The host cell of claim 12, which is *Saccharomyces* spp., *Kluyveromyces* spp., *Hansenula* spp., *Pichia* spp., or *Yarrowia* spp.

15. The host cell, according to claim 12, wherein the heterologous promoter is selected from the group consisting of the promoters of HXT7, PFK1, FBA1, PGK1, ADH1, TDH3 and a truncated promoter version of HXT7.

* * * * *

UNITED STATES PATENT AND TRADEMARK OFFICE
CERTIFICATE OF CORRECTION

Page 1 of 1

PATENT NO. : 8,993,301 B2
APPLICATION NO. : 14/231061
DATED : March 31, 2015
INVENTOR(S) : Boles et al.

It is certified that error appears in the above-identified patent and that said Letters Patent is hereby corrected as shown below:

In the Specification

Column 9,
Line 6, "(source of the data: U.S. Department of Energy:" should read --(source of the data: U.S. Department of Energy):--.

Column 9,
Line 16, "Sugar can bagasse" should read --Sugar cane bagasse--.

Column 18,
Line 25, "circument the problems" should read --circumvent the problems--.

Signed and Sealed this
Tenth Day of November, 2015

Michelle K. Lee
*Director of the United States Patent and Trademark Office*

UNITED STATES PATENT AND TRADEMARK OFFICE
CERTIFICATE OF CORRECTION

PATENT NO. : 8,993,301 B2
APPLICATION NO. : 14/231061
DATED : March 31, 2015
INVENTOR(S) : Eckhard Boles It is certified that error appears in the above-identified patent and that said Letters Patent is hereby corrected as shown below:

Title Page, Item (73) Assignee: "Butalco GmbH, Hünenberg (CH)" should read --Butalco GmbH, Fuerigen, SWITZERLAND--

Signed and Sealed this
Seventh Day of June, 2016

Michelle K. Lee
*Director of the United States Patent and Trademark Office*

SEQUENCE LISTING

<160> NUMBER OF SEQ ID NOS: 7

<210> SEQ ID NO 1
<211> LENGTH: 1704
<212> TYPE: DNA
<213> ORGANISM: Artificial
<220> FEATURE:
<223> OTHER INFORMATION: Gene sequence of the open harvest frame (ORF)
      of araBmut out of E. coli in one Codon optimized form

<400> SEQUENCE: 1

```
atggctattg ctattggttt ggacttcggt tctgactctg ttagagcttt ggctgttgac      60
tgtgcttctg gtgaagaaat tgctacctct gttgaatggt acccaagatg gcaaaagggt     120
caattctgtg acgctccaaa caaccaattc agacaccacc aagagacta cattgaatct     180
atggaagctg ctttgaagac cgttttggct gaattgtctg ttgaacaaag agctgctgtt     240
gttggtattg gtgttgactc taccggttct accccagctc aattgacgc tgacggtaac      300
gttttggctt tgagaccaga attcgctgaa acccaaacg ctatgttcgt tttgtggaag      360
aaccacaccg ctgttgaaga agctgaagaa attaccagat tgtgtcacgc tccaggtaac      420
gttgactact ctagatacat tggtggtatt tactcttctg aatggttctg ggctaagatt      480
ttgcacgtta ccagacaaga ctctgctgtt gctcaatctg ctgcttcttg gattgaattg      540
tgtgactggg ttccagcttt tgttgtctggt accaccagac acaagacat tagaagaggt     600
agatgttctg ctggtcacaa gtctttgtgg cacgaatctt ggggtggttt gccaccagct     660
tctttcttcg acgaattgga cccaattttg aacagacact tgccatctcc attgttcacc      720
gacacctgga ccgctgacat tccagttggt accttgtgtc cagaatgggc tcaaagattg      780
ggtttgccag aatctgttgt tatttctggt ggtgctttcg actgtcacat gggtgctgtt      840
ggtgctggtg ctcaaccaaa cgctttggtt aaggttattg gtacctctac ctgtgacatt      900
ttgattgctg acaagcaatc tgttggtgaa agagctgtta agggtatttg tggtcaagtt      960
gacggttctg ttgttccagg tttcattggt ttggaagctg gtcaatctgc tttcggtgac     1020
atttacgctt ggttcggtag agttttgtct tggccattgg aacaattggc tgctcaacac     1080
ccagaattga aggctcaaat taacgcttct caaaagcaat tgttgccagc tttgaccgaa     1140
gcttgggcta agaacccatc tttggaccac ttgccagttg tttggactg gttcaacggt     1200
agaagatctc caaacgctaa ccaaagattg aagggtgtta ttaccgactt gaacttggct     1260
accgacgctc cattgttgtt cggtggtttg attgctgcta ccgctttcgg tgctagagct     1320
attatggaat gtttcaccga ccaaggtatt gctgtcaaca cgttatggc tttgggtggt     1380
attgctagaa agaaccaagt tattatgcaa gcttgttgtg acgttttgaa cagaccattg     1440
caaattgttg cttctgacca atgttgtgct ttgggtgctg ctattttcgc tgctgttgct     1500
gctaaggttc acgctgacat tccatctgct caacaaaaga tggcttctgc tgttgaaaag     1560
accttgcaac aagatctga acaagctcaa agattcgaac aattgtacag aagataccaa     1620
caatgggcta tgtctgctga caacactac ttgccaacct ctgctccagc tcaagctgct     1680
caagctgttg ctaccttgta ataa                                            1704
```

<210> SEQ ID NO 2

<211> LENGTH: 699
<212> TYPE: DNA
<213> ORGANISM: Artificial
<220> FEATURE:
<223> OTHER INFORMATION: Gene sequence of the open harvest frame (ORF)
      of araD out of E. coli in one Codon optimized form

<400> SEQUENCE: 2

```
atgttggaag acttgaagag acaagttttg gaagctaact tggctttgcc aaagcacaac      60
ttggttacct tgacctgggg taacgtttct gctgttgaca gagaagagg tgttttcgtt     120
attaagccat ctggtgttga ctactctgtt atgaccgctg acgacatggt tgttgtttct     180
attgaaaccg gtgaagttgt tgaaggtacc aagaagccat cttctgacac cccaaccca      240
agattgttgt accaagcttt cccatctatt ggtggtattg ttcacaccca ctctagacac     300
gctaccattt gggctcaagc tggtcaatct attccagcta ccggtaccac ccacgctgac     360
tacttctacg gtaccattcc atgtaccaga agatgaccg acgctgaaat taacggtgaa     420
tacgaatggg aaaccggtaa cgttattgtt gaaaccttcg aaaagcaagg tattgacgct     480
gctcaaatgc aggtgttttt ggttcactct cacggtccat cgcttgggg taagaacgct     540
gaagacgctt tcacaacgc tattgtttg gaagaagttg cttacatggg tattttctgt     600
agacaattgg ctccacaatt gccagacatg caacaaacct tgttggacaa gcactacttg     660
agaaagcacg tgctaaggc ttactacggt caataataa                              699
```

<210> SEQ ID NO 3
<211> LENGTH: 1485
<212> TYPE: DNA
<213> ORGANISM: Artificial
<220> FEATURE:
<223> OTHER INFORMATION: Gene sequence of the open harvest frame (ORF)
      of araA out of Bacillus licheniformis in one Codon optimized form

<400> SEQUENCE: 3

```
atgattcaag ctaagaccca cgttttctgg ttcgttaccg ttctcaaca cttgtacggt        60
gaagaagctg ttcaagaagt tgaagaacac tctaagatga tttgtaacgg tttgaacgac      120
ggtgacttga gattccaagt tgaatacaag gctgttgcta cctctttgga cggtgttaga     180
aagttgttcg aagaagctaa cagagacgaa gaatgtgctg gtattattac ctggatgcac     240
accttctctc cagctaagat gtggattcca ggtttgtctg aattgaacaa gccattgttg     300
cacttccaca cccaattcaa cagagacatt ccatgggaca gattgacat ggacttcatg     360
aacattaacc aatctgctca cggtgacaga gaataccggtt tcattggtgc tagattgggt     420
attccaagaa aggttattgc tggttactgg gaagacagag aagttaagag atctattgac     480
aagtggatgt ctgctgctgt tgcttacatt gaatctagac acattaaggt tgctagattc     540
ggtgacaaca tgagaaacgt tgctgttacc gaaggtgaca agattgaagc tcaaattcaa     600
ttgggttggt ctgttgacgg ttacggtatt ggtgacttgg ttaccgaaat taacgctgtt     660
tctgaacaat ctttgtctga attgatttct gaatacgaag aattgtacga atggccagaa     720
ggtgaagctg ctagagaatc tgttaaggaa caagctagaa ttgaattggg tttgaagaga     780
ttcttgtctt ctggtggtta caccgctttc accaccacct cgaagactt gcacggtatg     840
aagcaattgc aggtttggc tgttcaaaga tgatggctg aaggttacgg tttcggtggt     900
gaaggtgact ggaagaccgc tgctttggtt agaatgatga agatgatggc tggtggtaag     960
gaaacctctt tcatggaaga ctacacctac cacttcgaac caggtaacga atgattttg     1020
ggttctcaca tgttggaagt tgtccatct attgctgaac acaagccaag aattgaagtt    1080
```

```
cacccattgt ctatgggtgc taaggacgac ccagctagat tggttttcga cggtattgct      1140
ggtccagctg tcaacgtttc tttgattgac ttgggtggta gattcagatt ggttattaac      1200
aaggttgaag ctgttaaggt tccacacgac atgccaaact tgccagttgc tagagttttg      1260
tggaagccac aaccatcttt gagaacctct gctgaagctt ggattttggc tggtggtgct      1320
caccacacct gtttgtctta ccaattgacc gctgaacaaa tgttggactg ggctgaaatg      1380
tctggtattg aagctgtttt gattaacaga gacaccacca ttttgaactt gagaaacgaa      1440
ttgaagtggt ctgaagctgc ttacagattg agaaagttct aataa                     1485
```

<210> SEQ ID NO 4
<211> LENGTH: 1482
<212> TYPE: DNA
<213> ORGANISM: Bacillus licheniformis

<400> SEQUENCE: 4

```
atgattcagg caaagacgca tgtgttttgg tttgtgacag gcagccagca tttatatggc        60
gaagaggcgg tacaagaggt agaagagcat tccaaaatga tctgcaacgg attaaatgac      120
ggagatttaa ggtttcaagt cgagtacaaa gcggtggcca cttcgctgga cggcgtcaga      180
aaactgtttg aagaggcgaa ccgggacgaa gagtgcgcag gcatcatcac ctggatgcat      240
acgttttcac cggccaaaat gtggattccc ggccttccg agctgaataa gccgctgctc       300
cattttcata cccagtttaa ccgggacatt ccgtgggata aaatcgacat ggatttcatg      360
aatattaatc agtctgccca cggcgaccgc gaatacggtt ttatcggagc gagattgggc      420
attcctcgaa aagtaatcgc cggatattgg gaagacagag aagtaaagcg ctcgatcgac      480
aaatggatga gcgcagcggt cgcatatatt gaaagccgcc atatcaaagt cgcccgattt      540
ggggacaaca tgcggaatgt ggcggtaaca gaaggagata gattgaagc gcagattcag      600 cttggctggt ctgtcgacgg atatggaatc ggcgatctcg tcacgagat caatgctgta      660 tcagaacaga gtctaagcga gctcatctcc gaatatgagg agctttatga gtggccggaa      720
ggcgaagcgg caagggaatc cgtcaaggag caggcgcgga ttgagcttgg attaaagcgc      780
tttctttcga gcggaggcta tacggccttt acgacaacct tgaagacct ccacggcatg       840 aagcagcttc cgggtttggc tgttcagcgg ctgatggctg aaggctatgg ctttggagga      900
gaaggagatt ggaaacggc tgcgcttgtc aggatgatga aatgatggc cggcggaaaa       960 gaaacgtcat ttatggagga ttacacgtac catttgaac cgggcaatga aatgatcctc       1020
ggctcccaca tgcttgaagt gtgccctcg attgccgaac acaaaccgag aattgaagtc      1080
catccgctgt caatgggtgc aaaggatgat ccggcgcggc tcgtgtttga cggaattgca      1140
ggtcctgcgg tcaatgtctc ccttattgat ttgggcggac gtttcaggct tgtcatcaat      1200
aaagtggaag ctgtgaaggt tccgcatgat atgccgaatc ttccggtggc gcgcgtactt      1260
tggaagcctc agccgtctct gagaacatcg gctgaagcgt ggattttggc tggcggtgct      1320
caccatacat gcctttcgta ccagctgaca gccgagcaga tgctcgattg gccgaaatg       1380 tcgggcattg aagcggtgtt gatcaatcgt gatacaacga ttttaaatct tcgcaatgaa      1440
ctcaaatgga gtgaagctgc atatcggctt cgcaagtttt aa                        1482
```

<210> SEQ ID NO 5
<211> LENGTH: 1467
<212> TYPE: DNA
<213> ORGANISM: Clostridium acetobutylicum

<400> SEQUENCE: 5

```
atgttagaaa ataaaaagat ggaattttgg tttgtagtag gaagtcaaca tttatatggt        60
gaagaggctt taaagaagt aagaaaaat tctgagacaa ttgtagatga attaaataaa         120
agtgctaatc ttccatataa aataatattt aaagatttag caacttctgc tgataaaata        180
aaggaaataa tgaaggaagt taactataga gatgaagtag caggagttat aacttggatg        240
catacgtttt ctccagctaa aatgtggata gcaggtacaa agatattaca aaacccttta        300
cttcattttg caactcaata taatgaaaat attccatgga aaacaataga tatggattat        360
atgaacttac atcaaagtgc tcatgggagat agagagtatg gatttattaa tgcaagactt        420
aaaaagcata ataaagttgt tgtaggatat tggaaggata agaagttca aaaacaagtt        480
tcagattgga tgaaggttgc tgcaggatat attgcaagtg aaagcataaa agttgcacgt        540
tttggtgata acatgcgtaa tgttgcagtt acagagggag ataaagtaga agctcaaata        600
caattcggat ggacagtaga ttactttggt ataggtgatt tagttgctga atggacaag         660
gtaagccaag atgaaataaa taaaacttat gaagaattta agatttata tattttagat         720
ccaggtgaaa atgatcctgc tttctatgag aaacaagtta agaacaaat caaaattgaa        780
ataggattaa gaaggttctt agaaaaagga aattataatg catttacaac aaactttgaa        840
gatctttatg gaatgaaaca gttacctgga cttgcagtac aacgtttaaa tgctgaaggc        900
tatggctttg caggcgaagg agactggaaa actgcagctt tagatagatt attaaaggtt        960
atgactaata atactgctac aggttttatg gaagattaca catatgaact tagtcgtgga       1020
aatgagaagg cattaggagc tcatatgctt gaagttgacc caacttttgc ttcagataaa       1080
ccaaaggtta ttgttaaacc actaggaatt ggagataag aagatccagc acgtttaatc       1140
tttaatggtt caacaggaaa aggtgtagca gtttcaatgc ttgatttagg aacacattat       1200
cgtttaataa taaacggact tacagcagtg aaaccagatg aagacatgcc aaacctacca       1260
gttgctaaaa tggtatggaa accagaacca aacttcattg aaggagttaa atcttggatt       1320
tatgcaggtg gcggacatca tacagtggtt tcactagaat taacagtaga acaggtttat       1380
gattggagtc gtatggtagg cttggaagct gtaataatag ataaggatac taaattaaga       1440
gatataatag aaaagacaac aaaataa                                          1467
```

<210> SEQ ID NO 6
<211> LENGTH: 493
<212> TYPE: PRT
<213> ORGANISM: Bacillus licheniformis

<400> SEQUENCE: 6

```
Met Ile Gln Ala Lys Thr His Val Phe Trp Phe Val Thr Gly Ser Gln
1               5                   10                  15

His Leu Tyr Gly Glu Glu Ala Val Gln Glu Val Glu Glu His Ser Lys
            20                  25                  30

Met Ile Cys Asn Gly Leu Asn Asp Gly Asp Leu Arg Phe Gln Val Glu
        35                  40                  45

Tyr Lys Ala Val Ala Thr Ser Leu Asp Gly Val Arg Lys Leu Phe Glu
    50                  55                  60

Glu Ala Asn Arg Asp Glu Glu Cys Ala Gly Ile Ile Thr Trp Met His
65                  70                  75                  80

Thr Phe Ser Pro Ala Lys Met Trp Ile Pro Gly Leu Ser Glu Leu Asn
                85                  90                  95

Lys Pro Leu Leu His Phe His Thr Gln Phe Asn Arg Asp Ile Pro Trp
```

```
                    100                 105                 110
Asp Lys Ile Asp Met Asp Phe Met Asn Ile Asn Gln Ser Ala His Gly
                115                 120                 125

Asp Arg Glu Tyr Gly Phe Ile Gly Ala Arg Leu Gly Ile Pro Arg Lys
            130                 135                 140

Val Ile Ala Gly Tyr Trp Glu Asp Arg Glu Val Lys Arg Ser Ile Asp
145                 150                 155                 160

Lys Trp Met Ser Ala Ala Val Ala Tyr Ile Glu Ser Arg His Ile Lys
                165                 170                 175

Val Ala Arg Phe Gly Asp Asn Met Arg Asn Val Ala Val Thr Glu Gly
            180                 185                 190

Asp Lys Ile Glu Ala Gln Ile Gln Leu Gly Trp Ser Val Asp Gly Tyr
        195                 200                 205

Gly Ile Gly Asp Leu Val Thr Glu Ile Asn Ala Val Ser Glu Gln Ser
    210                 215                 220

Leu Ser Glu Leu Ile Ser Glu Tyr Glu Glu Leu Tyr Glu Trp Pro Glu
225                 230                 235                 240

Gly Glu Ala Ala Arg Glu Ser Val Lys Glu Gln Ala Arg Ile Glu Leu
                245                 250                 255

Gly Leu Lys Arg Phe Leu Ser Ser Gly Tyr Thr Ala Phe Thr Thr
            260                 265                 270

Thr Phe Glu Asp Leu His Gly Met Lys Gln Leu Pro Gly Leu Ala Val
        275                 280                 285

Gln Arg Leu Met Ala Glu Gly Tyr Gly Phe Gly Gly Glu Gly Asp Trp
    290                 295                 300

Lys Thr Ala Ala Leu Val Arg Met Met Lys Met Met Ala Gly Gly Lys
305                 310                 315                 320

Glu Thr Ser Phe Met Glu Asp Tyr Thr Tyr His Phe Glu Pro Gly Asn
                325                 330                 335

Glu Met Ile Leu Gly Ser His Met Leu Glu Val Cys Pro Ser Ile Ala
            340                 345                 350

Glu His Lys Pro Arg Ile Glu Val His Pro Leu Ser Met Gly Ala Lys
        355                 360                 365

Asp Asp Pro Ala Arg Leu Val Phe Asp Gly Ile Ala Gly Pro Ala Val
    370                 375                 380

Asn Val Ser Leu Ile Asp Leu Gly Gly Arg Phe Arg Leu Val Ile Asn
385                 390                 395                 400

Lys Val Glu Ala Val Lys Val Pro His Asp Met Pro Asn Leu Pro Val
                405                 410                 415

Ala Arg Val Leu Trp Lys Pro Gln Pro Ser Leu Arg Thr Ser Ala Glu
            420                 425                 430

Ala Trp Ile Leu Ala Gly Gly Ala His His Thr Cys Leu Ser Tyr Gln
        435                 440                 445

Leu Thr Ala Glu Gln Met Leu Asp Trp Ala Glu Met Ser Gly Ile Glu
    450                 455                 460

Ala Val Leu Ile Asn Arg Asp Thr Thr Ile Leu Asn Leu Arg Asn Glu
465                 470                 475                 480

Leu Lys Trp Ser Glu Ala Ala Tyr Arg Leu Arg Lys Phe
                485                 490

<210> SEQ ID NO 7
<211> LENGTH: 488
<212> TYPE: PRT
<213> ORGANISM: Clostridium acetobutylicum
```

-continued

```
<400> SEQUENCE: 7

Met Leu Glu Asn Lys Lys Met Glu Phe Trp Phe Val Val Gly Ser Gln
1               5                   10                  15

His Leu Tyr Gly Glu Glu Ala Leu Lys Glu Val Arg Lys Asn Ser Glu
            20                  25                  30

Thr Ile Val Asp Glu Leu Asn Lys Ser Ala Asn Leu Pro Tyr Lys Ile
        35                  40                  45

Ile Phe Lys Asp Leu Ala Thr Ser Ala Asp Lys Ile Lys Glu Ile Met
50                  55                  60

Lys Glu Val Asn Tyr Arg Asp Glu Val Ala Gly Val Ile Thr Trp Met
65                  70                  75                  80

His Thr Phe Ser Pro Ala Lys Met Trp Ile Ala Gly Thr Lys Ile Leu
                85                  90                  95

Gln Lys Pro Leu Leu His Phe Ala Thr Gln Tyr Asn Glu Asn Ile Pro
            100                 105                 110

Trp Lys Thr Ile Asp Met Asp Tyr Met Asn Leu His Gln Ser Ala His
        115                 120                 125

Gly Asp Arg Glu Tyr Gly Phe Ile Asn Ala Arg Leu Lys Lys His Asn
130                 135                 140

Lys Val Val Gly Tyr Trp Lys Asp Lys Glu Val Gln Lys Gln Val
145                 150                 155                 160

Ser Asp Trp Met Lys Val Ala Ala Gly Tyr Ile Ala Ser Glu Ser Ile
                165                 170                 175

Lys Val Ala Arg Phe Gly Asp Asn Met Arg Asn Val Ala Val Thr Glu
            180                 185                 190

Gly Asp Lys Val Glu Ala Gln Ile Gln Phe Gly Trp Thr Val Asp Tyr
        195                 200                 205

Phe Gly Ile Gly Asp Leu Val Ala Glu Met Asp Lys Val Ser Gln Asp
210                 215                 220

Glu Ile Asn Lys Thr Tyr Glu Glu Phe Lys Asp Leu Tyr Ile Leu Asp
225                 230                 235                 240

Pro Gly Glu Asn Asp Pro Ala Phe Tyr Glu Lys Gln Val Lys Glu Gln
                245                 250                 255

Ile Lys Ile Glu Ile Gly Leu Arg Arg Phe Leu Glu Lys Gly Asn Tyr
            260                 265                 270

Asn Ala Phe Thr Thr Asn Phe Glu Asp Leu Tyr Gly Met Lys Gln Leu
        275                 280                 285

Pro Gly Leu Ala Val Gln Arg Leu Asn Ala Glu Gly Tyr Gly Phe Ala
290                 295                 300

Gly Glu Gly Asp Trp Lys Thr Ala Ala Leu Asp Arg Leu Leu Lys Val
305                 310                 315                 320

Met Thr Asn Asn Thr Ala Thr Gly Phe Met Glu Asp Tyr Thr Tyr Glu
                325                 330                 335

Leu Ser Arg Gly Asn Glu Lys Ala Leu Gly Ala His Met Leu Glu Val
            340                 345                 350

Asp Pro Thr Phe Ala Ser Asp Lys Pro Lys Val Ile Val Lys Pro Leu
        355                 360                 365

Gly Ile Gly Asp Lys Glu Asp Pro Ala Arg Leu Ile Phe Asn Gly Ser
370                 375                 380

Thr Gly Lys Gly Val Ala Val Ser Met Leu Asp Leu Gly Thr His Tyr
385                 390                 395                 400

Arg Leu Ile Ile Asn Gly Leu Thr Ala Val Lys Pro Asp Glu Asp Met
```

```
                    405                     410                     415
Pro Asn Leu Pro Val Ala Lys Met Val Trp Lys Pro Glu Pro Asn Phe
            420                     425                 430

Ile Glu Gly Val Lys Ser Trp Ile Tyr Ala Gly Gly Gly His His Thr
        435                 440                 445

Val Val Ser Leu Glu Leu Thr Val Glu Gln Val Tyr Asp Trp Ser Arg
    450                 455                 460

Met Val Gly Leu Glu Ala Val Ile Ile Asp Lys Asp Thr Lys Leu Arg
465                 470                 475                 480

Asp Ile Ile Glu Lys Thr Thr Lys
                485
```